(12) United States Patent
Wagtmann et al.

(10) Patent No.: US 8,551,483 B2
(45) Date of Patent: Oct. 8, 2013

(54) METHODS OF TREATING VIRAL INFECTIONS BY ADMINISTERING KIR2DL-BINDING ANTIBODIES

(75) Inventors: Peter Andreas Nicolai Reumert Wagtmann, Rungsted Kyst (DK); Francois Romagne, La Ciotat (FR); Joakim Glamann, Gentofte (DK)

(73) Assignees: Innate Pharma S.A.S., Marseille (FR); Novo Nordisk A/S, Bagsvaerd (DK)

(*) Notice: Subject to any disclaimer, the term of this patent is extended or adjusted under 35 U.S.C. 154(b) by 1153 days.

(21) Appl. No.: 11/813,399

(22) PCT Filed: Jan. 6, 2006

(86) PCT No.: PCT/EP2006/050071
§ 371 (c)(1),
(2), (4) Date: May 21, 2008

(87) PCT Pub. No.: WO2006/072624
PCT Pub. Date: Jul. 13, 2006

(65) Prior Publication Data
US 2009/0035305 A1      Feb. 5, 2009

Related U.S. Application Data

(60) Provisional application No. 60/646,717, filed on Jan. 25, 2005.

(30) Foreign Application Priority Data

Jan. 6, 2005   (DK) .................................. 2005 00027

(51) Int. Cl.
*A61K 39/395* (2006.01)
*C07K 16/00* (2006.01)

(52) U.S. Cl.
USPC ................ 424/144.1; 530/388.73; 530/389.6; 424/208.1

(58) Field of Classification Search
None
See application file for complete search history.

(56) References Cited

FOREIGN PATENT DOCUMENTS

| JP | 2006-528626 | 12/2006 |
|---|---|---|
| WO | WO 2005/003168 A2 | 1/2005 |
| WO | WO 2005/003172 A2 | 1/2005 |
| WO | WO 2005/009465 A1 | 2/2005 |

OTHER PUBLICATIONS

Ahmad, A., and R. Ahmad. 2003. HIV's evasion of host's NK cell response and novel ways of its countering and boosting anti-HIV immunity. Current HIV Res. 1:295-307.*
Trkola, A., et al. 2005. Delay of HIV-1 rebound after cessation of antiretroviral therapy through passive transfer of human neutralizing antibodies. Nat. Med. 11(6):615-622.*
Bansal, G. P. 2007. A summary of the workshop on passive immunization using monoclonal antibodies for HIV/AIDS, held at the National Institute of Allergy and Infectious Diseases, Bethesda, Mar. 10, 2006. Biol. 35:367-371.*
Montefiori, D. C. 2005. Neutralizing antibodies take a swipe at HIV in vivo. Nat. Med. 11(6):593-594.*
Jahrling, P. B., et al. 2007. Ebola hemorrhagic fever: evaluation of passive immunotherapy in nonhuman primates. J. Infect. Dis. 196(S2):S400-S403.*
Geisbert, T. W., et al. 2002. Evaluation in nonhuman primates of vaccines against Ebola virus. Emerg. Infect. Dis. 8(5):503-507.*
Mohamadzadeh, M., et al. 2007. How Ebola and Marburg viruses battle the immune system. Nat. Rev. Immunol. 7:556-567.*
Kleymann, G. 2005. Agents and strategies in development for improved management of herpes simplex virus infection and disease. Expert Opin. Investig. Drugs 14(2):135-161.*
De Paoli, P. 2004. Human herpesvirus 8: an update. Microb. Infect. 6:238-335.*
Xu, R., et al. 2009. Phase I evaluation of the safety and pharmacokinetics of a single-dose intravenous injections of a murine monoclonal antibody against Hantaan virus in healthy volunteers. Antimicrob. Agents Chemother. 53(12):5055-5059.*
Conry, S. J., et al. 2009. Impaired plasmacytoid dendritic cell (PDC)-NK cell activity in viremic human immunodeficiency virus infection attributable to impairments in both PDC and NK cell function. J. Virol. 83(21):11175-11187.*
Brunetta, E., et al. 2010. Pathologic natural killer cell subset redistribution in HIV-1 infection: new insights in pathophysiology and clinical outcome. J. Leukocyte Biol. 88(6):1119-1130.*
Reed, D. S., et al. 2004. Depletion of peripheral blood T lymphocytes and NK cells during the course of Ebola hemorrhagic fever in cynomolgus macaques. Vir. Immunol. 17(3):390-400.*
Lusso, P. 2006. HHV-6 and the immune system: mechanisms of immunomodulation and viral escape. J. Clin. Virol. 37(S1):S4-S10.*
Yuan, W., et al. 2006. Herpes simplex virus evades natural killer T cell recognition by suppressing CD1d recycling. Nat. Immunol. 7(8):835-842.*
Ahmad, A. et al., "HIV's Evasion of Host's NK Cell Response and Novel Ways of its Countering and Boosting Anti-HIV Immunity", Current HIV Research, 2003, vol. 1, pp. 295-307.
Ahmad, R. et al., "Modulation of Expression of the MHC Class I-Binding Natural Killer Cell Receptors, and NK Activity in Relation to Viral Load in HIV-Infected/AIDS Patients", Journal of Medical Virology, 2001, vol. 65, pp. 431-440.

(Continued)

*Primary Examiner* — Jeffrey S. Parkin
(74) *Attorney, Agent, or Firm* — Robin L. Teskin; LeClairRyan, a Professional Corporation

(57) ABSTRACT

Described are methods of treating viral disease using compounds that block inhibitory NK cell receptors, thereby reducing their inhibition of NK cell cytotoxicity in killing infected target cells. In one embodiment, the compound is an antibody binding, for example, one or more of the human KIR2DL1, KIR2DL2, and KIR2DL3 receptors. In another embodiment, the method further comprises administering a therapeutic antibody or fusion protein which binds an antigen expressed on cells infected with the virus.

7 Claims, 4 Drawing Sheets

(56) References Cited

OTHER PUBLICATIONS

De Maria, A. et al., "Expression of HLA Class I-Specific Inhibitory Natural Killer Cell Receptors in HIV-Specific Cytolytic T Lymphocytes: Impairment of Specific Cytolytic Functions", Proc. Natl. Acad. Sci. USA, 1997, vol. 94, pp. 10285-10288.

Shin, J-S. et al., "Monoclonal Antibodies with Various Reactivity to p58 Killer Inhibitory Receptors", Hybridoma, 1999, vol. 18, No. 6, pp. 521-527.

Sirianni, M.C. et al., "Distribution of the Natural Killer-Related Receptor for HLA-C During Highly Active Antiretroviral Therapy for Human Immunodeficiency Virus Infection", Human Immunology, 2001, vol. 62, pp. 1328-1334.

Spaggiari, G.M. et al., "Soluble HLA Class I Induces NK Cell Apoptosis Upon the Engagement of Killer-Activating HLA Class I Receptors Through FasL-Fas Interaction", Blood, 2001, vol. 100, No. 12, pp. 4098-4107.

Spaggiari, G.M. et al., "Soluble HLA Class I Molecules Induce Natural Killer Cell Apoptosis Through the Engagement of CD8: Evidence for a Negative Regulation Exerted by Members of the Inhibitory Receptor Superfamily", Blood, 2002, vol. 99, No. 5, pp. 1706-1714.

Ward, J.P. et al., "HLA-C and HLA-E Reduce Antibody-Dependent Natural Killer Cell-Mediated Cytotoxicity of HIV-Infected Primary T Cell Blasts", AIDS, 2004, vol. 18, pp. 1769-1779.

Takiguchi, M, "Research on Elucidation of Cellular Immunity Factor for Development of Vaccine Effective for Prevention of AIDS and Activation Thereof," Report of International Research of Granted Project, Japan Health Science Foundation, Sep. 30, 2004, pp. 75-83.

Mavilio, D, et al. "Natural killer cells in HIV-1 infection: Dichotomous effects of viremia on inhibitory and activating receptors and their functional correlates," PNAS vol. 100, No. 25, Dec. 9, 2003, pp. 15011-15016. 8 pages.

Martin, M., et al. "Epistatic interaction between KIR3DS1 abd HLA-B delays the progression to AIDS," Nature Genetics, vol. 31, Aug. 2002, pp. 429-434. 7 pages.

\* cited by examiner ered to deplete target cells, particularly diseased cells such as virally-infected cells, tumor cells or other pathogenic cells. Such antibodies are typically monoclonal antibodies, of immunoglobulin gamma (IgG) species, typically with human IgG1 or IgG3 Fc portion. These antibodies can be native or recombinant antibodies, humanized mouse antibodies (i.e. comprising functional domains from various species, typically Fc portion of human or non-human primate origin, and variable region or complementary determining region (CDR) of mouse origin). Alternatively, the monoclonal antibody can be fully human through immunization in human Ig locus transgenic mice or obtained through cDNA libraries derived from human cells. A particular example of such therapeutic antibodies is rituximab (Mabthera®, Rituxan®), which is a chimeric anti-CD20 monoclonal antibody made with human γ1 and κ constant regions (therefore with human IgG1 Fc portion) linked to murine variable domains conferring CD20 specificity. In the past few years, rituximab has considerably modified the therapeutical strategy against B lymphoproliferative malignancies, particularly non-Hodgkin's lymphomas (NHL). Other examples of humanized IgG1 antibodies include alemtuzumab (Campath-1H®), which is used in the treatment of B cell malignancies or trastuzumab (Hercep-

SEQUENCE LISTING

```
<160> NUMBER OF SEQ ID NOS: 4

<210> SEQ ID NO 1
<211> LENGTH: 450
<212> TYPE: PRT
<213> ORGANISM: Homo sapiens

<400> SEQUENCE: 1

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Phe Tyr
            20                  25                  30

Ala Ile Ser Trp Val Arg Gln Ala Pro Gly Gln Gly Leu Glu Trp Met
        35                  40                  45

Gly Gly Phe Ile Pro Ile Phe Gly Ala Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Ile Pro Ser Gly Ser Tyr Tyr Asp Tyr Asp Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190
```

```
Thr Val Pro Ser Ser Ser Leu Gly Thr Lys Thr Tyr Thr Cys Asn Val
    195                 200                 205

Asp His Lys Pro Ser Asn Thr Lys Val Asp Lys Arg Val Glu Ser Lys
    210                 215                 220

Tyr Gly Pro Pro Cys Pro Ser Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
                260                 265                 270

Asp Pro Glu Val Gln Phe Asn Trp Tyr Val Asp Gly Val Glu Val His
                275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Gln Glu Glu Met Thr Lys Asn Gln Val Ser Leu
                355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
                420                 425                 430

Glu Ala Leu His Asn His Tyr Thr Gln Lys Ser Leu Ser Leu Ser Leu
    435                 440                 445

Gly Lys
    450

<210> SEQ ID NO 2
<211> LENGTH: 214
<212> TYPE: PRT
<213> ORGANISM: Homo sapiens

<400> SEQUENCE: 2

Glu Ile Val Leu Thr Gln Ser Pro Val Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Met Tyr
                85                  90                  95

Thr Phe Gly Gln Gly Thr Lys Leu Glu Ile Lys Arg Thr Val Ala Ala
                100                 105                 110
```

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 42
<212> TYPE: DNA
<213> ORGANISM: Artificial
<220> FEATURE:
<223> OTHER INFORMATION: Primer

<400> SEQUENCE: 3
ggaattccag gaggaattta aaatgcatga gggagtccac ag              42

<210> SEQ ID NO 4
<211> LENGTH: 36
<212> TYPE: DNA
<213> ORGANISM: Artificial
<220> FEATURE:
<223> OTHER INFORMATION: Primer

<400> SEQUENCE: 4
cccaagcttg ggttatgtga cagaaacaag cagtgg                     36
```

METHODS OF TREATING VIRAL INFECTIONS BY ADMINISTERING KIR2DL-BINDING ANTIBODIES

CROSS-REFERENCE TO RELATED APPLICATIONS

This application is a 35 U.S.C. §371 national stage application of International Patent Application PCT/EP2006/050071 (published as WO 2006/072624), filed Jan. 6, 2006, which claims priority of Danish Patent Application PA 2005 00027, filed Jan. 6, 2005; this application further claims priority under 35 U.S.C. §119 of U.S. Provisional Application 60/646,717, filed Jan. 25, 2005.

FIELD OF THE INVENTION

The present invention relates to methods and compositions for treatment of viral infections such as HIV (Human Immunodeficiency Virus), and HCV (Hepatitis C Virus). More particularly, the invention relates to the use of a monoclonal antibody (mAb) specific for one or more human Killer Ig-like receptors (KIR) for treatment of these and other viral diseases. In a particular embodiment, the invention relates to the use of such mAbs in the treatment of HIV patients who have undergone HAART therapy. In another particular embodiment, the invention relates to the use of a therapeutic antibody specific for a surface molecule expressed on virus-infected cells in combination with a mAb (or other compound) that binds to and blocks the inhibitory KIR receptors of natural killer cells and allow a potentiation of natural killer cell cytotoxicity in mammalian subjects in order to enhance the efficiency of the treatment in human subjects, particularly through an increase of the antibody dependent cellular cytotoxicity (ADCC) mechanism leading to eradication of virally infected cells.

BACKGROUND OF THE INVENTION

Various therapeutic strategies in human beings are based on the use of therapeutic antibodies. This includes, for instance, the use of therapeutic antibodies devel- tin®), which is used in the treatment of breast cancer. Additional examples of therapeutic antibodies under development are disclosed in the art.

The mechanism of action of therapeutic antibodies developed to depletion of cells bearing the antigen specifically recognized by the antibody. This depletion can be mediated through at least four mechanisms: ADCC, complement dependent lysis, phagocytosis and direct antitumor effects, for example inhibition of tumor growth by mAb-mediated blockade of growth-receptor signalling.

While these antibodies represent a novel approach to human therapy, particularly in treatment of neoplasms, they do not always exhibit a strong efficacy. For instance, while rituximab, alone or in combination with chemotherapy was shown to be effective in the treatment of both low-intermediate and high-grade NHL, 30% to 50% of patients with low grade NHL have no clinical response to rituximab. It has been suggested that the level of CD20 expression on lymphoma cells, the presence of high tumor burden at the time of treatment or low serum rituximab concentrations may explain the lack of efficacy of rituximab in some patients. Nevertheless, the actual causes of treatment failure remain largely unknown. We have previously discovered that the tumor cell-killing efficacy of rituximab can be enhanced by boosting ADCC by natural killer (NK) cells. One mechanism by which NK cells can kill target cells is by ADCC, when a mAb binds with the antigen-specific portion to an antigen on a target cell, and at the same time the Fc portion of the mAb binds to an Fc-receptor (called CD16) on NK cells. This leads to activation of CD16 on the NK cell, which triggers activation of the NK cell cytolytic machinery. However, NK cells also express inhibitory receptors, such as KIR, which deliver negative signals to the NK cells, thereby balancing out positive signals for example transduced via CD16. We have found that by blocking the inhibitory KIR receptors, using mAb that bind to KIR and prevent its function, the stimulatory signalling through CD16 can be enhanced, leading to increased NK killing of tumor target cells, in the presence of mAbs that can simultaneously bind to an antigen on the target and to CD16 on NK cells.

WO2005003168 and WO2005003172 describe the use of cross-reactive anti-KIR antibodies for treating, e.g., cancer, an infectious disease or an immune disorder.

WO2005009465 describes the use of an antibody that blocks an NK cell inhibitory receptor and a therapeutic antibody that can be bound by CD16 to treat cancer, an infectious disease, or an immune disorder.

The present invention provides a method of enhancing the NK-mediated ADCC response towards virus-infected cells in the presence of therapeutic mAbs specific for antigens expressed on virally infected cells, as a treatment of viral infections, for example HIV-infections.

SUMMARY OF THE INVENTION

The present invention discloses novel approaches to treat HIV and to enhance the efficacy of therapeutic antibodies for the treatment of viral infections. These approaches are based on a specific subgroup of HIV patients which are suitable for treatment with compounds targeting NK cell inhibitory receptors, and on an increase of the ADCC mechanism in vivo, when therapeutic antibodies are injected. Indeed, the present invention now provides novel compositions and methods that overcome the current difficulty related to the low efficacy of therapeutic antibodies in the treatment of viral infections. It is shown in the present invention that NK cells of an individual have poor therapeutic mAb (monoclonal antibodies) mediated ADCC because it is inhibited by inhibitory receptors on NK cells. Preferably, an increase of the ADCC mechanism is achieved by the administration of compounds that block the inhibitory receptor of natural killer cells and allow a potentiation of natural killer cell cytotoxicity in mammalian subjects. Preferably the compound is an antibody or a fragment thereof. The antibodies react with an inhibitory receptor of NK cells, i.e. Killer inhibitory receptor (KIR or CD94/NKG2A/C) molecules on NK cells, and neutralize their inhibitory signals, thereby increasing their ADCC activity.

Accordingly, in one aspect, the present invention provides a method of treatment of a viral disease caused by HIV in a human subject in need thereof, comprising administering to the human subject a first compound that blocks an inhibitory receptor of an NK cell, wherein the human subject has been treated with highly active antiretroviral therapy (HAART). In one embodiment, the compound is an antibody binding to KIR2DL1, KIR2DL2, and KIR2DL3, and blocks KIR2DL1-, KIR2DL2-, and KIR2DL3-mediated inhibition of NK cell cytotoxicity. In another embodiment, the antibody competes with monoclonal antibody DF200 in binding to at least one of KIR2DL1, KIR2DL2, and KIR2DL3, or with monoclonal antibody 1-7F9 in binding to at least one of KIR2DL1, KIR2DL2, and KIR2DL3. In a particular embodiment, the antibody is monoclonal antibody 1-7F9. In another embodiment, the human subject may have been treated with HAART for a sufficient period of time to achieve an HIV plasma level below a predetermined level prior to administering the first compound. In another embodiment, the method further comprises administering to the subject a second compound which is a therapeutic antibody or fusion protein binding an antigen expressed on an HIV-infected cell. In a particular embodiment, the second compound is a therapeutic antibody.

In another aspect, the invention provides for a method of treatment of a viral disease in a human subject in need thereof, comprising (a) administering to the subject a first compound that blocks an inhibitory receptor of an NK cell, and (b) administering to the subject a second compound which is a therapeutic antibody or fusion protein binding an antigen expressed on a virus infected cell. In one embodiment, the viral disease is caused by HIV (Human Immunodeficiency Virus), RSV (Respiratory syncytial virus), CMV (Cytomegalovirus), Ebola virus, Hepatitis A virus, Hepatitis B virus, Hepatitis C virus, Epstein-Barr virus, varicella zos-ter virus (VZV), Hantaan virus, influenza virus, Herpes simplex virus (HSV), Human herpes virus 6 (HHV-6), human herpes virus 8 (HHV-8), Human papilloma virus, or Parvovirus. In separate particular embodiments, the viral disease is caused by HIV or by Hepatitis C virus.

In one embodiment, the second compound is a therapeutic antibody. In another embodiment, the second compound is an antibody or fusion protein comprising an Fc portion of a human IgG1 or IgG3 antibody. In one embodiment, the first compound is an antibody or a fragment thereof. In a particular embodiment, at least one of the first and second compounds is a monoclonal antibody. In another particular embodiment, at least one of the first and second compounds is a human, humanized or chimeric antibody.

The first compound may bind, for example, at least one of a CD94, an NKG2A/C, a KIR2DL and a KIR3DL human receptor and reduce the inhibition of NK cell cytotoxicity mediated by the human receptor to which it binds. In one embodiment, the first compound binds a common determinant of at least two KIR2DL human receptors and reduces the inhibition of NK cell cytotoxicity mediated by the KIR2DL human receptors to which it binds. For example, the first compound may bind a common determinant of KIR2DL1, KIR2DL2, and KIR2DL3 human receptors and prevent KIR2DL1-, KIR2DL2-, KIR2DL3-mediated inhibition of NK cell cytotoxicity. The first compound may, for example, be an antibody competing with monoclonal antibody DF200 or monoclonal antibody 1-7F9 in binding to at least one of KIR2DL1, KIR2DL2, and KIR2DL3.

In one embodiment, the first and second compounds are simultaneously administered to the subject. In another embodiment, the second compound is administered into the subject within four weeks of the administration of the first compound.

The antigen may be selected from, e.g., the group consisting of CD3, CD28, CD4, CCR5, gp120, and gp41.

In another aspect, the invention also provides a method for treatment of a viral disease in a human subject in need thereof, comprising administering to the subject a compound that blocks an inhibitory receptor of an NK cell.

DETAILED DESCRIPTION OF THE INVENTION

Figure 1:
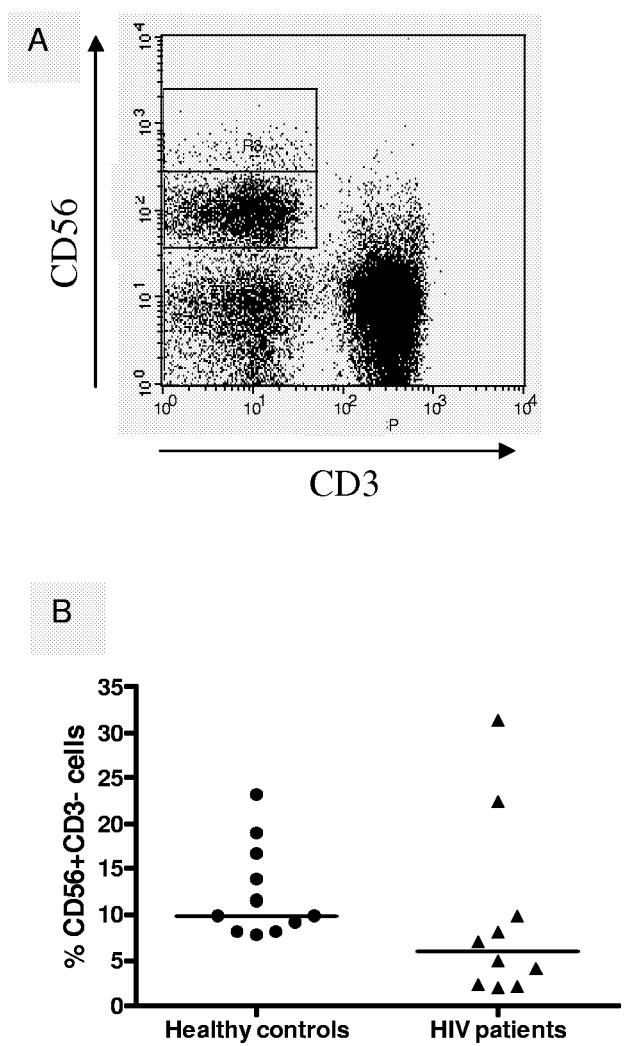
FIG. 1. (A) NK-cells were defined as all CD56+CD3– cells in the lymphocyte gate. Boxes show CD56dim cells (lower box) as well as CD56bright cells (upper box). (B) The proportion of NK-cells of all lymphocytes for healthy controls and HAART treated HIV-1 infected patients is shown, with a line indicating the median. No significant difference was seen.

This invention is based, in part, on the discovery that HIV patients treated with HAART may be more suitable for treatment with anti-KIR antibodies than patients with very active disease (see Example 5). The invention is also based, in part, on the discovery that antibodies against NK cell inhibitory receptors may improve the efficacy of therapeutic antibodies against viral antigens, particularly therapeutic antibodies that can be bound by CD16, by enhancing the ADCC response against such therapeutic antibodies.

Based on the data in Example 5, two important conclusions can be drawn:

1) There is a group of HIV-infected patients, namely patients treated with HAART, that harbor functional, activatable NK cells which express functional, inhibitory KIR, that regulate the killing activity of said NK cells, and these KIR can be blocked by anti-KIR mAbs, thereby inducing lysis by those NK cells towards targets that express HLA-C. By contrast, one previously reported characteristic of HIV-infected cells is that they down-regulate (or abrogate) expression of HLA-A and -B to avoid killing by T cells, while retaining expression of HLA-C, thereby avoiding killing by NK cells.

2) Infection of target cells by HIV does not cause reduction in expression of activating ligands that are required to triggering the activating receptors on NK cells.

Together these new findings suggest that endogenous NK cells in at least HAART patients may kill HIV-infected cells when KIR or another NK cell inhibitory receptor is blocked using, e.g., an antibody capable of reducing KIR-mediated blocking of NK cell cytotoxicity.

In one embodiment, it is, for example, envisaged that patients are treated as early as possible with HAART until viral load is below a predetermined level or below detection level for a predetermined period of time, e.g., at least 1, 2, 4, 8, or 20 weeks. The predetermined level could be, for example, a viral load below detection level, a viral load below about 50 RNA copies/ml, a viral load below about 100 RNA copies/ml, or a viral load below about 200 RNA copies/ml. Once viral load has gone below the predetermined level, or once viral load has been below the predetermined level for the predetermined period of time, treatment with a compound capable of reducing the NK cell inhibitory activity of an NK cell inhibitory receptor is initiated. Such compounds are described herein.

The present invention also provides a means to increase the efficiency of the therapeutic antibodies. The invention more specifically discloses that the use of a compound, such as an antibody or a fragment thereof, that blocks the inhibitory receptor of a NK cell, can significantly increase the efficiency of therapeutic antibodies. Indeed, the inventors demonstrate that NK-mediated killing of virus-infected cells can be greatly enhanced in the presence of an antibody directed against a NK cell inhibitory receptor.

Therefore, the invention concerns a method of treatment of a disease in a subject in need thereof comprising:

a) administering to the subject a compound, such as an antibody or a fragment thereof, that blocks one or more inhibitory receptors of a NK cell; and, b) administering to the subject a therapeutic antibody, specific for an antigen expressed on virus-infected cells.

The therapeutic antibody can bind to CD16 on NK-cells, preferably through its Fc region.

Preferably, the therapeutic antibody has a human IgG1 or an IgG3 Fc portion, particularly a monoclonal antibody or a fragment thereof, further preferably a humanized, human or chimeric antibody or a fragment thereof.

The compound, preferably an antibody or a fragment thereof, that block the inhibitory receptor of a NK cell can be administered to the subject before, simultaneously with, or after, the administration of the therapeutic antibody. The mode of administration of the different antibodies depends on their bioavailability and pharmacokinetics. In one aspect of the invention, the therapeutic antibody is administrated within 0 to four weeks of the administration of the compound, preferably an antibody or a fragment thereof, that block the inhibitory receptor of a NK cell, in another aspect within two weeks, or within one week, and in a further aspect within 5 or 2 days. In one aspect, the therapeutic antibody is administrated before or simultaneously with the compound, such as an antibody or a fragment thereof, that block the inhibitory receptor of a NK cell.

In a further aspect, the invention concerns a method of increasing ADCC in a subject receiving a therapeutic antibody treatment, the method comprising administering to the subject prior to, simultaneously, or after the administration of the therapeutic antibody, an amount sufficient to increase ADCC of a compound, such as an antibody or a fragment thereof, that blocks the inhibitory receptor of a NK cell. The therapeutic antibody can be bound by CD16 on NK cells, preferably through its Fc region. Preferably, the therapeutic antibody has a human IgG1 or an IgG3 Fc portion, particularly a monoclonal antibody or a fragment thereof, further preferably a human, humanized or chimeric antibody or a fragment thereof.

In an additional aspect, the invention concerns a method of increasing the efficiency of a therapeutic antibody treatment in a subject, the method comprising administering to the subject prior to, simultaneously or after the administration of the therapeutic antibody an effective amount of a compound, such as an antibody or a fragment thereof, that blocks the inhibitory receptor of a NK cell sufficiently to increase the efficiency of the therapeutic antibody. The therapeutic antibody can be bound by CD16, preferably through its Fc region. Preferably, the therapeutic antibody has a human IgG1 or IgG3 Fc portion, particularly a monoclonal antibody, further preferably a human, humanized or chimeric antibody.

Within the context of the present invention, a subject or patient includes any mammalian subject or patient, more preferably a human subject or patient.

More specifically, the invention discloses methods of treatment of a subject in which a compound, such as an antibody or a fragment thereof, that blocks the inhibitory receptor of a NK cell are co-administered with the therapeutic antibody to the subject. The invention provides co-administration with the therapeutic antibodies directed specifically against viral infection.

The invention concerns a pharmaceutical composition comprising a therapeutic antibody and a compound, such as an antibody or a fragment thereof, that blocks the inhibitory receptor of a NK cell. The invention also concerns a kit comprising a therapeutic antibody against virus-infected cells and a compound, such as an antibody or a fragment thereof, that blocks the inhibitory receptor of a NK cell.

The invention concerns the use of a compound, such as an antibody or a fragment thereof, that blocks the inhibitory receptor of a NK cell for increasing the efficiency of a treatment with a therapeutic antibody directed against virus-infected cells, or for increasing ADCC in a subject submitted to a treatment with a therapeutic antibody.

The invention also concerns the use of a compound, such as an antibody or a fragment thereof, that blocks the inhibitory receptor of a NK cell and of a therapeutic antibody for the preparation of a drug for treating a disease. More particularly, the treatment of the disease requires the depletion of the targeted cells, and the disease is viral infection.

In a particular aspect, the invention concerns a method of treatment of a subject in need thereof comprising:

a) administering to the subject a compound, such as an antibody or a fragment thereof, that blocks the inhibitory receptor of a NK cell; and, b) administering to the subject a therapeutic antibody which is specific for HIV-infection.

The therapeutic antibody is capable of forming an immune complex. Preferably, the therapeutic antibody can be bound by CD16 receptor present on NK cells, preferably through its Fc region. In a preferred embodiment, the therapeutic antibody has a human or non-human primate IgG1 or IgG3 Fc portion. Preferably, the therapeutic antibody is a monoclonal antibody or a fragment or a derivative thereof, more preferably a humanized, human or chimeric antibody or a fragment thereof.

NK cells retain CD16, the low-affinity receptor for IgG. The simultaneous binding of IgG to an antigen on a target cell, and CD16 on NK cells, results in activation of NK cells, and killing of the target bound by the antibody. Co-administration of anti-KIR mAbs together with mAbs specific for receptors in HIV-infected targets, such as an anti-CD4 mAb, will enhance NK-mediated ADCC. Exemplary anti-CD4 mAbs for use in the present invention include, but are not limited to, trx I (TolerRx) and HuMax CD4 (Genmab). Other CD4 mAbs can be produced according to known methods in the art, or obtained from commercial sources.

In an embodiment of the invention, preferred therapeutic mAbs specific for antigens on HIV-infected cells include mAbs specific for surface molecules on T cells or specific for ligands that are encoded by the HIV virus and expressed selectively on infected cells. Such therapeutic mAbs be specific for surface molecules such as: CD3, CD28, CD4, CCR5, gp120, gp41. Exemplary anti-CD3, CD28, CD4, CCR5, gp120, and gp41 mAbs for use in the present invention include, but are not limited to, trx4 (TolerRx), anti-HIV-1 gp120 antibody described in Science, 1994, vol 266, p 1024-1027; and Anti HIV-1 gp 41 antibody described in AIDS Res Hum Retroviruses 1994, vol 10, p 1651-1658. Other suitable antibodies can be produced according to known methods in the art, or obtained from commercial sources.

In another embodiment of the invention preferred therapeutic antibodies include those that are specific for antigens encoded by other viruses. These viruses include RSV (Respiratory syncytial Virus), CMV (Cytomegalovirus), Ebola virus, Hepatitis A virus, Hepatitis B virus, Hepatitis C virus, Epstein-Barr virus, varicella zoster virus (VZV), Hantaan virus, influenza virus, Herpes simplex virus (HSV), Human herpes virus 6 (HHV-6), human herpes virus 8 (HHV-8) Human papilloma virus, and Parvovirus.

In another embodiment of the invention preferred therapeutic antibodies include those that are specific for cellular antigens expressed by virus infected cells. For HCV these include antibodies that are specific for cellular antigens expressed by infected liver cells. The F and G protein of RSV, the E1 and E2 protein of HCV, the gp1 and gp 2 antigens of Ebolavirus, the L1 protein of human papilloma virus (HPV).

In one aspect, the invention provides a method of treating HIV (Human Immunodeficiency Virus), RSV (Respiratory syncytial Virus), CMV (Cytomegalovirus), Ebola virus, Hepatitis A virus, Hepatitis B virus, Hepatitis C virus, Epstein-Barr virus, varicella zoster virus (VZV), Hantaan virus, influenza virus, Herpes simplex virus (HSV), Human herpes virus 6 (HHV-6), human herpes virus 8 (HHV-8) Human papilloma virus, and Parvovirus, comprising administering to a patient in need thereof a therapeutically efficient amount of an antibody, or a fragment thereof, that blocks the inhibitory receptor of a NK cell.

In one aspect, the method of treating a viral disease caused by one of the vira mentioned above comprises administering to the same patient a therapeutically efficient amount of a further anti-viral agent. Examples of such agents are Against Herpes simplex, varicella zoster virus (VSV) infection: Aciclovir, famciclovir, valaciclovir, penciclovir.

Against CMV infection: Ganciclovir, valganciclovir.

Against retrovirus infection (e.g HIV-1): Lamivudin, zidovudin, emtricitabin, abacavir, tenofovir, didanosin, stavudin, efavirenz, nevirapin, amprenavir, indinavir, saquinavir, ritonavir, lopinavir, atazanavir, nelfinavir, enfuvirtid.

Against influenza virus infection: Oseltamivir.

Against chronic hepatitis B virus infection: Adefovir, lamivudin

Against chronic hepatitis C virus infection: Ribavirin, interferon-alpha, pegylated interferon alpha.

In one embodiment, the patient has been treated with HAART prior to administration of an antibody that blocks an inhibitory receptor of an NK cell. HAART therapy consists of a cocktail of anti-viral drugs. The classes include, e.g., nucleosidal reverse transcriptase inhibitors (NRTI), non-nucleosidal reverse transcriptase inhibitors (NNRTI) and protease inhibitors (PI). Usually 2 to 4 drugs from preferentially more than one class are combined to reduce viral load to almost non-detectable levels. HAART therapies are often combinations or "cocktails" of two or more antiretroviral agents. R. M. Gulick, "Current antiretroviral therapy: an overview", Qual. Life Res. 6:471-474 (1997); K. Henry et al., "Antiretroviral therapy for HIV infection. Heartening Successes mixed with continuing challenges", Postgrad. Med. 102:100-107 (1997); C. B. Hicks, "Update on antiretroviral therapy", Radiol. Clin. North Am. 35:995-1005 (1997); R. H. Goldschmidt, "Antiretroviral drug treatment for HIV/AIDS", Am. Fam. Physician, 54:574-580 (1996). Drugs used in HAART regimens include the nucleoside analogs AZT, stavudine (d4T), and 3TC; nevirapine (a non-nucleoside reverse transcriptase inhibitor, which may be abbreviated NVP), and protease inhibitors such as RTV, SQV, IDV, and nelfinavir. HAART using these treatments may reduce plasma loads of active HIV virus in HIV-1-positive patients to undetectable amounts (below about 50 copies/ml), apparently without the threat of developing resistant strains of HIV. M. Baiter, "HIV Survives Drug Onslaught by Hiding Out in T Cells," Science 278:1227 (Nov. 14, 1997). This document and all documents cited to herein, are incorporated by reference as if fully reproduced below. HAART products, dosing schedules and common side effects are also given in appended Tables I to III of U.S. patent application publication 20050191702, hereby incorporated by reference in its entirety.

In an embodiment of the invention induction of ADCC response is by receptor Fc fusion proteins, wherein the Fc part binds to CD16 and the receptor binds a ligand on the T-cells. This ligand could be a CD-2-Fc protein binding LFA-3 on T cells.

Preferably, the compound, such as an antibody or a fragment thereof, that blocks the inhibitory receptor of a NK cell binds at least one of KIR or CD94 or NKG2A/C human receptors and inhibits the related KIR2DL, KIR3DL and/or NKG2A/C-mediated inhibition of NK cell cytotoxicity. Preferably, KIR2DL human receptor is selected from the group consisting of KIR2DL1, KIR2DL2, KIR2DL3 human receptors and KIR3DL human receptor is selected from the group consisting of KIR3DL1 and KIR3DL2. In a preferred embodiment, the compound, such as an antibody or a fragment thereof, that blocks the inhibitory receptor of a NK cell binds a common determinant of two or more KIR2DL human receptors and prevents KIR2DL-mediated inhibition of NK cell cytotoxicity. More preferably, the antibody binds a common determinant of KIR2DL1, KIR2DL2, KIR2DL3 human receptors and prevents KIR2DL1-, KIR2DL2-, KIR2DL3-mediated inhibition of NK cell cytotoxicity. In a particular embodiment, the compound, such as an antibody or a fragment thereof, that blocks the inhibitory receptor of a NK cell inhibits the binding of a HLA-C allele molecule having a Lys residue at position 80 to a human KIR2DL1 receptor, and the binding of a HLA-C allele molecule having an Asn residue at position 80 to human KIR2DL2 and KIR2DL3 receptors. In another particular embodiment, the antibody or a fragment thereof that blocks the inhibitory receptor of a NK cell binds to the same epitope as monoclonal antibody DF200 produced by hybridoma DF200. Optionally, this antibody or a fragment thereof, competes with monoclonal antibody DF200 produced by hybridoma DF200 for binding to a KIR receptor at the surface of a human NK cell. In one preferred embodiment, this antibody is monoclonal antibody DF200 produced by hybridoma DF200. The hybridoma producing antibody DF200, registration no. CNCM 1-3224, registered 10 Jun. 2004, Collection Nationale de Cultures de Microorganismes, Institut Pasteur, 25 Rue du Docteur Roux, F-75724 Paris Cedex 15, France.

In another particular embodiment, the antibody or a fragment thereof that blocks the inhibitory receptor of a NK cell binds to the same epitope as monoclonal antibody 1-7F9, a human monoclonal antibody that binds KIR2DL1, KIR2DL2, and KIR2DL3 and reduces or blocks inhibition of KIR-mediated NK cell cytotoxicity, as described in, e.g., WO2005003168. The VH and VL sequences of 1-7F9 are described in SEQ ID NOS:1 and 2, respectively. Optionally, the antibody or a fragment thereof competes with 1-7F9 (i.e., an antibody comprising the heavy (H) and light (L) chain sequences of 1-7F9), for binding to a KIR receptor at the surface of a human NK cell. In one preferred embodiment, this antibody is 1-7F9, i.e., a monoclonal antibody that comprises the H and L sequences of 1-7F9.

In a preferred embodiment, the antibody or a fragment thereof that blocks the inhibitory receptor of a NK cell is a monoclonal antibody, a fragment or a derivative thereof. More preferably, the antibody is a humanized, human or chimeric antibody or a fragment thereof. The fragment or a derivative thereof is preferably selected from a Fab fragment, a Fab'$_2$ fragment, a CDR and a ScFv.

Therapeutic Antibody

Within the context of this invention, the term "therapeutic antibody or antibodies" designates more specifically any antibody that functions to deplete target cells in a patient. Specific examples of such target cells include tumor cells, virus-infected cells, allogenic cells, pathological immunocompetent cells (e.g., B lymphocytes, T lymphocytes, antigen-presenting cells, etc.) involved in allergies, autoimmune diseases, allogenic reactions, etc., or even healthy cells (e.g., endothelial cells in an anti-angiogenic therapeutic strategy). Most preferred target cells within the context of this invention are tumor cells and virus-infected cells. The therapeutic antibodies may, for instance, mediate a cytotoxic effect or a cell lysis, particularly by antibody-dependant cell-mediated cytotoxicity (ADCC). ADCC requires leukocyte receptors for the Fc portion of IgG (FcγR) whose function is to link the IgG-sensitized antigens to FcγR-bearing cytotoxic cells and to trigger the cell activation machinery. Therefore, the therapeutic antibody is capable of forming an immune complex. For example, an immune complex can be a tumor target (i.e. cells) covered by therapeutic antibodies. More particularly, the antibody can be bound by CD16, preferably through its Fc region.

The therapeutic antibodies may by polyclonal or, preferably, monoclonal. They may be produced by hybridomas or by recombinant cells engineered to express the desired variable and constant domains. The antibodies may be single chain antibodies or other antibody derivatives retaining the antigen specificity and the lower hinge region or a variant thereof. These may be polyfunctional antibodies, recombinant antibodies, humanized antibodies, fragments or variants thereof. The fragment or a derivative thereof is preferably selected from a Fab fragment, a Fab'2 fragment, a CDR and a ScFv. Therapeutic antibodies are specific for surface antigens, e.g., membrane antigens. In the present invention, preferred membrane antigens are those expressed on for HIV-infected cells. These include CD4, CD3, and CD28. The therapeutic antibodies have preferably human or non human primate IgG1 or IgG3 Fc portion, more preferably human IgG1.

Nk Cell-Regulating Antibody

NK cell activity is regulated by a complex mechanism that involves both stimulating and inhibitory signals. Accordingly, effective NK cell-mediated therapy can be achieved both by a stimulation of these cells or a neutralization of inhibitory signals.

NK cells are negatively regulated by major histocompatibility complex (MHC) class I-specific inhibitory receptors (Kärre et al., 1986; Öhlén et al, 1989; the disclosure of which is incorporated herein by reference). These specific receptors bind to polymorphic determinants of major histocompatibility complex (MHC) class I molecules or HLA and inhibit natural killer (NK) cell lysis. In humans, a family of receptors termed killer Ig-like receptors (KIRs) recognize groups of HLA class I alleles.

There are several groups of KIR receptors, including KIR2DL, KIR2DS, KIR3DL and KIR3DS. KIR receptors having two Ig domains (KIR2D) identify HLA-C allotypes: KIR2DL2 (formerly designated p58.1) or the closely related gene product KIR2DL3 recognizes an epitope shared by group 2 HLA-C allotypes (Cw1, 3, 7, and 8), whereas KIR2DL1 (p58.2) recognizes an epitope shared by the reciprocal group 1 HLA-C allotypes (Cw2, 4, 5, and 6). The recognition by KIR2DL1 is dictated by the presence of a Lys residue at position 80 of HLA-C alleles. KIR2DL2 and KIR2DL3 recognition is dictated by the presence of a Asn residue at position 80. Importantly the great majority of HLA-C alleles have either an Asn or a Lys residue at position 80. One KIR with three Ig domains, KIR3DL1 (p70), recognizes an epitope shared by HLA-Bw4 alleles. Finally, a homodimer of molecules with three Ig domains KIR3 DL2 (p140) recognizes HL A-A3 and -A11.

Although KIRs and other class-I inhibitory receptors (Moretta et al, 1997; Valiante et al, 1997; Lanier, 1998; the disclosure of which is incorporated herein by reference) may be co-expressed by NK cells, in any given individual's NK repertoire, there are cells that express a single KIR and thus, the corresponding NK cells are blocked only by cells expressing a specific class I allele group.

In the present invention, the term "a compound or compounds, preferably antibody or antibodies or a fragment thereof, that block(s) the inhibitory receptor of a NK cell" refers to a compound, such as an antibody or a fragment thereof, specific for at least one NK cells inhibitory receptor, i.e. KIR or NKG2A/C of NK cells, and neutralizing inhibitory signals of the KIR or NKG2A/C. Preferably, the compound, such as an antibody or a fragment thereof, is able to block the interaction between HLA and an inhibitory receptor of a NK cell. The antibodies may by polyclonal or, preferably, monoclonal. They may be produced by hybridomas or by recombinant cells engineered to express the desired variable and constant domains. The antibodies may be single chain antibodies or other antibody derivatives retaining the antigen specificity and the lower hinge region or a variant thereof such as a Fab fragment, a Fab'2 fragment, a CDR and a ScFv. These may be polyfunctional antibodies, recombinant antibodies, humanized antibodies, or variants thereof.

Preferably, the compound, such as an antibody or a fragment thereof, that blocks the inhibitory receptor of a NK cell is a compound, such as an antibody or a fragment thereof, that neutralizes the inhibitory signal of at least one inhibitory receptor selected in the group consisting of KIR2DL2, KIR2DL 3, KIR2DL1, KIR3DL1, KIR3DL2, NKG2A and NKG2C. More preferably, the compound, such as an antibody or a fragment thereof, that blocks the inhibitory receptor of a NK cell is a compound, such as an antibody or a fragment thereof, that neutralizes the inhibitory signal of KIR2DL2, KIR2DL3 and/or KIR2DL1.

The invention also contemplates the use of a combination of several compounds, preferably antibodies or a fragment thereof, that block different inhibitory receptors of NK cells. Preferably, compounds, preferably antibodies or a fragment thereof, that block inhibitory receptors of NK cells are specific of an inhibitory receptor selected from KIR2DL1, KIR2DL2, KIR2DL3, KIR3DL1, KIR3DL2, NKG2A and NKG2C and are able to inhibit the related KIR- or NKG2A/C-mediated inhibition of NK cell cytotoxicity. For example, the compounds that block inhibitory receptors of NK cells can comprise an antibody having specificity for KIR2DL1 and another having specificity for KIR2DL2 and/or KIR2DL3. More preferably, the combination of compounds that block inhibitory receptors of NK cells is able to inhibit the KIR2DL1-, KIR2DL2-, and KIR2DL3-mediated inhibition of NK cell cytotoxicity.

For example, monoclonal antibodies specific for KIR2DL1 have been shown to block the interactions between KIR2DL1 and HLA-Cw4 allotypes, as well as similar HLA-C allotypes belonging to the same group as Cw4 (Morena et al., J Exp Med. 1993; 178(2):597-604; the disclosure of which is incorporated herein by reference). In another example, monoclonal antibodies against KIR2DL2/3 have also been described that block the interactions of KIR2DL2/3 with HLACw3 (or the like) allotypes (Morena et al., 1993, supra). Anti NKG2A antibodies have been shown to block the inhibitory interaction between NKG2A and HLA-E.

Optionally, the antibody can be selected from the group consisting of GL183 (KIR2DL2/3/S2-specific, available from Immunotech, France and Beckton Dickinson, USA); EB6 (KIR2DL1/s1-specific, available from Immunotech, France and Beckton Dickinson, USA); AZ138 (KIR3DL1-specific, available from Moretta et al, Univ. Genova, Italy); Q66 (KIR3DL2-specific, available from Immunotech, France); Z270 (NKG2A-specific, available from Immunotech, France); P25 (NKG2A/C-specific, available from Moretta et al, Univ. Genova, Italy); and DX9, Z27 (KIR3DL1-specific, available from Immunotech, France and Beckton Dickinson, USA).

In a preferred aspect, the invention uses monoclonal antibodies, as well as fragments and derivatives thereof, wherein the antibody, fragment or derivative cross reacts with several KIR or NKG2A/C receptors at the surface of NK cells and neutralizes their inhibitory signals. More preferably, the invention uses a monoclonal antibody that binds a common determinant of human KIR2DL receptors and inhibit the corresponding inhibitory pathway. More specifically, the invention uses a monoclonal antibody that binds KIR2DL1 and KIR2DL2/3 receptors at the surface of human NK cells and inhibits KIR2DL1- and KIR2DL2/3-mediated inhibition of NK cell cytotoxicity. The antibody specifically inhibits binding of HLA-C molecules to KIR2DL1 and KIR2DL2/3 receptors. More preferably, the antibody facilitates NK cell activity in vivo.

Because KIR2DL1 and KIR2DL3 (or KIR2DL2) can form a molecular complex with most of the HLA-C allotypes, respectively group 1 HLA-C allotypes and group 2 HLA-C allotypes, antibodies against KIR2DL1 and KIR2DL3 may be used to increase the efficiency of a therapeutic antibody in most human individuals, typically in about 90% of human individuals or more.

In a particular object of this invention, the antibody that blocks the inhibitory receptor of a NK cell is a monoclonal antibody, wherein the antibody binds a common determinant of KIR2DL human receptors and inhibits KIR2DL-mediated inhibition of NK cell cytotoxicity. The antibody more specifically binds to the same epitope as monoclonal antibody DF200 produced by hybridoma DF200 and/or competes with monoclonal antibody DF200 produced by hybridoma DF200 for binding to a KIR receptor at the surface of a human NK cell.

In a specific embodiment, the monoclonal antibody is monoclonal antibody DF200 produced by hybridoma DF200.

Within the context of this invention a "common determinant" designates an antigenic determinant or epitope that is shared by several members of the human KIR2DL receptor group. The determinant or epitope may represent a peptide fragment or a conformational epitope shared by the members. In a specific embodiment, the common determinant comprises an epitope recognized by monoclonal antibody DF200.

Within the context of this invention, the term antibody that "binds" a common determinant designates an antibody that binds the determinant with specificity and/or affinity, e.g., that essentially does not bind with high affinity or with specificity other unrelated motifs or determinant or structures at the surface of human NK cells. More particularly, the binding of a monoclonal antibody according to this invention to the determinant can be discriminated from the binding of the antibody to another epitope or determinant.

These compounds, preferably antibodies, are thus "neutralizing" or "inhibitory" compounds, preferably antibodies, in the sense that they block, at least partially, the inhibitory signalling pathway mediated by an NK cells inhibitory receptor, i.e. KIR or NKG2A/C receptors. More importantly, this inhibitory activity can be displayed with respect to several types of KIR or NKG2A/C receptors, so that these compounds, preferably antibodies, may be used in various subjects with high efficacy. Inhibition of KIR- or NKG2A/C-mediated inhibition of NK cell cytotoxicity can be assessed by various assays or tests, such as binding or cellular assays. In a specific variant, the inhibitory activity is illustrated by the capacity of the compound, such as an antibody, to reconstitute lysis of KIR or NKG2A/C positive NK clones, respectively, on HLA-C or HLA-E positive targets. In another specific embodiment, the compound, such as an antibody, is defined as inhibiting the binding of HLA-C molecules to KIR2DL1 and KIR2DL3 (or the closely related KIR2DL2) receptors, further preferably as its capacity to alter:

the binding of a HLA-C molecule selected from Cw1, Cw3, Cw7, and Cw8 (or of a HLA-c molecule having an Asn residue at position 80) to KIR2DL2/3; and the binding of a HLA-C molecule selected from Cw2, Cw4, Cw5 and Cw6 (or of a HLA-c molecule having a Lys residue at position 80) to KIR2DL1.

In another variant, the inhibitory activity of a compound of this invention, such as an antibody, can be assessed in a cell based cytotoxicity assay, as disclosed in the examples.

In another variant, the inhibitory activity of a compound of this invention, such as an antibody, can be assessed in a cytokine-release assay.

The compounds of this invention, preferably antibodies, may exhibit partial inhibitory activity, e.g., partially reduce the KIR2DL-mediated inhibition of NK cell cytotoxicity. Most preferred compounds are able to inhibit at least 20%, preferably at least 30%, 40% or 50% or more of the KIR- or NKG2A/C-mediated inhibition of NK cell toxicity, preferably of the KIR2DL-mediated inhibition of NK cell cytotoxicity. Alternatively, preferred compounds of this invention, preferably antibodies, are able to induce the lysis of matched or HLA compatible or autologous target cell population, i.e., cell population that would not be effectively lysed by NK cells in the absence of the antibody. Accordingly, compounds of this invention may also be defined as facilitating NK cell activity in vivo.

The invention also contemplates embodiments in which the compounds that block the inhibitory receptor of a NK cell are fragments and derivatives of such a monoclonal antibody having substantially the same antigen specificity, including, without limitation, a Fab fragment, a Fab'2 fragment, a CDR and a ScFv. Furthermore, the monoclonal antibody may be humanized, human, or chimeric (e.g. a bispecific or functionalised antibody).

The antibodies that block the inhibitory receptor of a NK cell according to the invention may be produced by a variety of techniques known per se in the art. Typically, they are produced by immunization of a non-human animal with an immunogen comprising a KIR or NKG2A/C polypeptide, and collection of spleen cells (to produce hybridomas by fusion with appropriate cell lines). Methods of producing monoclonal antibodies from various species may be found in Harlow et al (Antibodies: A laboratory Manual, CSH Press, 1988; the disclosure of which is incorporated herein by reference). More specifically, these methods comprise immunizing a non-human animal with the antigen, followed by a recovery of spleen cells which are then fused with immortalized cells, such as myeloma cells. The resulting hybridomas produce the monoclonal antibodies and can be selected by limiting dilutions to isolate individual clones. Antibodies may also be produced by selection of combinatorial libraries of immunoglobulins, as disclosed for instance in Ward et al (1989); the disclosure of which is incorporated herein by reference.

Preferred antibodies that block the inhibitory receptor of a NK cell according to the invention are prepared by immunization with an immunogen comprising a KIR2DL polypeptide, more preferably a human KIR2DL polypeptide. The KIR2DL polypeptide may comprise the full length sequence of a human KIR2DL polypeptide, or a fragment or derivative thereof, typically an immunogenic fragment, i.e., a portion of the polypeptide comprising an epitope, preferably a T or B cell epitope. Such fragments typically contain at least 7 consecutive amino acids of the mature polypeptide sequence, even more preferably at least 10 consecutive amino acids thereof. They are essentially derived from the extra-cellular domain of the receptor.

In a most preferred embodiment, the immunogen comprises a wild-type human KIR2DL polypeptide in a lipid membrane, typically at the surface of a cell. In a specific embodiment, the immunogen comprises intact NK cells, particularly intact human NK cells, optionally treated or lysed.

The antibodies that block the KIR2DL receptors of NK cells can be produced by methods comprising:

immunizing a non-human mammal with an immunogen comprising a KIR2DL polypeptide;

preparing monoclonal antibodies from the immunized animal, wherein the monoclonal antibodies bind the KIR2DL polypeptide, selecting monoclonal antibodies of (b) that cross react with at least two different serotypes of KIR2DL polypeptides, and selecting monoclonal antibodies of (c) that inhibit KIR2DL-mediated inhibition of NK cells.

The order of steps (c) and (d) can be changed. Optionally, the method may further comprise additional steps of making fragments or derivatives of the monoclonal antibody, as disclosed below. In preferred embodiment, the non-human animal is a mammal, such as a rodent (e.g., mouse, rat, etc.), bovine, porcine, horse, rabbit, goat, sheep, etc. Also, the non-human mammal may be genetically modified or engineered to produce "human" antibodies.

In another variant, the method comprises:

selecting, from a library or repertoire, a monoclonal antibody or a fragment or derivative thereof that cross reacts with at least two different serotypes of KIR2DL polypeptides, and selecting an antibody of (a) that inhibits KIR2DL-mediated inhibition of NK cells.

The repertoire may be any (recombinant) repertoire of antibodies or fragments thereof, optionally displayed by any suitable structure (e.g., phage, bacteria, synthetic complex, etc.). Selection of inhibitory antibodies may be performed as disclosed above and further illustrated in the examples.

Similar methods can be used for the preparation of antibodies that block a KIR3DL or a or NKG2A/C receptor of NK cells.

Competition with Cross-Reactive and/or Neutralizing Antibodies

In another aspect, the invention provides antibodies that block the inhibitory receptor of a NK cell characterized by the ability to compete with cross-reactive and/or neutralizing antibodies that block the inhibitory receptor of a NK cell according to the invention for binding to cognate KIRs and/or to bind to the same antigenic determinant region/epitope as such known antibodies, for use in the methods of the invention. For example, in one aspect the invention provides an anti-KIR Antibody characterized by its ability to compete with antibody NKVSF1, 1-7F9, and/or antibody DF200.

The phrase "competes with" when referring to a particular monoclonal antibody (e.g. DF200, NKVSF1, etc.) means that the Anti-KIR Antibody competes with the referenced antibody or other molecule in a binding assay using either recombinant KIR molecules or surface expressed KIR molecules. For example, if an anti-KIR antibody detectably reduces binding of DF200 to a KIR molecule normally bound by DF200 in a binding assay, the anti-KIR Anti-body can be said to "compete" with DF200. An anti-KIR Antibody that "competes" with DF200 may compete with DF200 for binding to the KIR2DL1 human receptor, the KIR2DL2/3 human receptor, or both KIR2DL1 and KIR2DL2/3 human receptors.

Antibodies that compete with DF200, 1-7F9, and/or NKVSF1 can be identified using known screening assays. A number of such assays are routinely practiced and well known in the art (see, e.g., U.S. Pat. No. 5,660,827, which is specifically incorporated herein by reference). Protocols based on, e.g., ELISAs, radio-immunoassays, Western blotting, and the use of BIACORE analysis are suitable for use in such competition studies.

One can, e.g., pre-mix the control antibody (e.g., DF200, NKVSF1, or 1-7F9) with varying amounts of the test antibody (e.g., in ratios of about 1:1, 1:2, 1:10 or about 1:100) for a period of time prior to applying to a KIR antigen sample. Alternatively, the control and varying amounts of test antibody can simply be added separately and admixed during exposure to the KIR antigen sample. As long as one can distinguish bound from free antibodies (e.g., by using separation or washing techniques to eliminate un-bound antibodies) and control antibody from the test antibody (e.g., by using species specific or isotype specific secondary antibodies or by specifically labelling the control antibody with a detectable label) one will be able to determine if the test antibody reduce the binding of the control antibody to the different KIR2DL antigens, indicating that the test antibody recognizes substantially the same epitope as the control. The binding of the (labeled) control antibody in the presence of a completely irrelevant antibody (that does not bind KIR) can serve as the control high value. The control low value can be obtained by incubating the labeled control antibody with the same but unlabelled control antibody, where competition would occur and reduce binding of the labeled antibody. In a test assay, a significant reduction in labeled antibody reactivity in the presence of a test antibody is indicative of a test antibody that recognizes substantially the same epitope, i.e., one that competes with the labeled control antibody. For example, any test antibody that reduces the binding of control antibody to one or both of KIR2DL1 and KIR2DL3 antigens by at least about 50%, such as at least about 60%, or more preferably at least about 70% (e.g., about 65-100%), at any ratio of control:test antibody between about 1:1 or 1:10 and about 1:100 is considered to be an antibody that competes with the control.

Competition can also be assessed by, for example, flow cytometry. In such a test, cells bearing a given KIR can be incubated first with a control antibody, and then with the test antibody labeled with a fluorochrome or biotin. The antibody is said to compete with control antibody if the binding obtained upon pre-incubation with saturating amount of control antibody is about 80%, preferably about 50%, about 40% or less (e.g., about 30%) of the binding (as measured by mean of fluorescence) obtained by the test antibody without preincubation with control antibody. Alternatively, an antibody is said to compete with the control antibody if the binding obtained with a labeled control antibody (by a fluorochrome or biotin) on cells preincubated with saturating amount of test antibody is about 80%, preferably about 50%, about 40%, or less (e.g., about 30%) of the binding obtained without preincubation with the test antibody.

A simple competition assay in which a test antibody is pre-adsorbed and applied at saturating concentration to a surface onto which either KIR2DL1 or KIR2DL2/3, or both, are immobilized also may be advantageously employed. The surface in the simple competition assay is preferably a BIACORE chip (or other media suitable for surface plasmon resonance analysis). The binding of a control antibody to the KIR-coated surface is measured. This binding to the KIR-containing surface of the control antibody alone is compared with the binding of the control antibody in the presence of a test antibody. A significant reduction in binding to the KIR2DL1 and KIR2DL2/3-containing surface by the control antibody in the presence of a test antibody indicates that the test antibody recognizes substantially the same epitope as the control antibody such that the test antibody "competes" with the control antibody. Any test antibody that reduces the binding of control antibody to both of KIR2DL1 and KIR2DL2/3 antigens by at least about 20% or more, at least about 40%, at least about 50%, at least about 70%, or more, can be considered to be an antibody that competes with the control antibody. Preferably, such test antibody will reduce the binding of the control antibody to each of at least the KIR2DL1, 2, and 3 antigens by at least about 50% (e.g., at least about 60%, at least about 70%, or more). It will be appreciated that the order of control and test antibodies can be reversed; i.e. the control antibody can be first bound to the surface and then the test antibody is brought into contact with the surface thereafter in a competition assay. Preferably, the antibody having higher affinity for KIR2DL1 and KIR2DL2/3 antigens is bound to the KIR2DL1 and KIR2DL2/3-containing surface first, as it will be expected that the decrease in binding seen for the second antibody (assuming the antibodies are competing) will be of greater magnitude. Further examples of such assays are provided in the Examples herein, and in e.g., Saunal and Regenmortel, (1995) J. Immunol. Methods 183: 33-41, the disclosure of which is incorporated herein by reference.

Determination of whether an antibody or other agent binds to the same or substantially the same epitope region as, e.g., DF200, NKVSF1, or 1-7F9, can be carried out using methods known to the person skilled in the art. In an example of epitope mapping/characterization methods, an epitope region for an anti-KIR antibody may be determined by epitope "foot-printing" using chemical modification of the exposed amines/carboxyls in the KIR2DL1 or KIR2DL2/3 protein. One specific example of such a foot-printing technique is the use of HXMS (hydrogen-deuterium exchange detected by mass spectrometry) wherein a hydrogen/deuterium exchange of receptor and ligand protein amide protons, binding, and back exchange occurs, wherein the backbone amide groups participating in protein binding are protected from back exchange and therefore will remain deuterated. Relevant regions can be identified at this point by peptic proteolysis, fast microbore high-performance liquid chromatography separation, and/or electrospray ionization mass spectrometry. See, e.g., Ehring H, Analytical Biochemistry, Vol. 267 (2) pp. 252-259 (1999) and/or Engen, J. R. and Smith, D. L. (2001) Anal. Chem. 73, 256A-265A. Another example of a suitable epitope identification technique is nuclear magnetic resonance epitope mapping (NMR), where typically the position of the signals in two-dimensional NMR spectres of the free antigen and the antigen complexed with the antigen binding peptide, such as an antibody, are compared. The antigen typically is selectively isotopically labeled with 15N so that only signals corresponding to the antigen and no signals from the antigen binding peptide are seen in the NMR-spectrum. Antigen signals originating from amino acids involved in the interaction with the antigen binding peptide typically will shift position in the spectres of the complex compared to the spectres of the free antigen, and the amino acids involved in the binding can be identified that way. See, e.g., Ernst Schering Res Found Workshop. 2004; (44):149-67; Huang et al, Journal of Molecular Biology, Vol. 281 (1) pp. 61-67 (1998); and Saito and Patterson, Methods. 1996 June; 9(3):516-24.

Epitope mapping/characterization also can be performed using mass spectrometry methods. See, e.g., Downward, J Mass Spectrom. 2000 April; 35(4):493-503 and Kiselar and Downard, Anal Chem. 1999 May 1; 71 (9):1792-801.

Protease digestion techniques also can be useful in the context of epitope mapping and identification. Antigenic determinant-relevant regions/sequences can be determined by protease digestion, e.g by using trypsin in a ratio of about 1:50 to KIR2DL1 or KIR2DL2/3 o/n digestion at 37° C. and pH 7-8, followed by mass spectrometry (MS) analysis for peptide identification. The peptides protected from trypsin cleavage by the anti-KIR antibody can subsequently be identified by comparison of samples subjected to trypsin digestion and samples incubated with antibody and then subjected to digestion by e.g. trypsin (thereby revealing a foot print for the antibody). Other enzymes like chymotrypsin, pepsin, etc., also or alternatively can be used in similar epitope characterization methods. Moreover, enzymatic digestion can provide a quick method for analyzing whether a potential antigenic determinant sequence is within a region of the KIR2DL1 in the context of a KIR-binding agent. If the polypeptide is not surface exposed, it is most likely not relevant in terms of immunogenicity/antigenicity. See, e.g., Manca, Ann Ist Super Sanita. 1991; 27(1):15-9 for a discussion of similar techniques.

Site-directed mutagenesis is another technique useful for elucidation of a binding epitope. For example, in "alanine-scanning", each residue within a protein segment is re-placed with an alanine residue, and the consequences for binding affinity measured. If the mutation leads to a significant reduction in binding affinity, it is most likely involved in binding. Monoclonal antibodies specific for structural epitopes (i.e., antibodies which do not bind the unfolded protein) can be used to verify that the alanine-replacement does not influence over-all fold of the protein. See, e.g., Clackson and Wells, Science 1995; 267:383-386; and Wells, Proc Natl Acad Sci USA 1996; 93:1-6.

Electron microscopy can also be used for epitope "footprinting". For example, Wang et al., Nature 1992; 355:275-278 used coordinated application of cryoelectron microscopy, three-dimensional image reconstruction, and X-ray crystallography to determine the physical footprint of a Fab-fragment on the capsid surface of native cowpea mosaic virus.

Other forms of "label-free" assay for epitope evaluation include surface plasmon resonance (SPR, BIACORE) and reflectometric interference spectroscopy (RifS). See, e.g., Fägerstam et al., Journal Of Molecular Recognition 1990; 3:208-14; Nice et al., J. Chromatogr. 1993; 646:159-168; Leipert et al., Angew. Chem. Int. Ed. 1998; 37:3308-3311; Kröger et al., Biosensors and Bioelectronics 2002; 17:937-944.

Although often related, describing a protein in terms of competition with a reference binding protein versus the ability of the protein to bind to the same or substantially similar epitope as a reference protein in some cases imply significantly different biological and physiochemical properties. Competition between binding proteins implies that the test Anti-KIR Antibody binds to an epitope that at least partially overlaps with an epitope bound by an anti-KIR antibody or is located near enough to such an epitope so that such an Anti-KIR Antibody competes with known anti-KIR antibodies due to steric hindrance. A large Anti-KIR Antibody, such as an anti-KIR Antibody that consists of or comprises an antibody, may compete with a reference anti-KIR antibody, without binding to the same or similar epitope due to the large size of the antibodies. Such a competing Anti-KIR Antibody can be useful in blocking interactions associated with the same antigenic determining region as the reference anti-KIR antibody even though it binds a different antigenic determinant.

Composition and Administration

The invention concerns a composition comprising at least one compound, such as an antibody or a fragment thereof, that blocks the inhibitory receptor of a NK cell and a therapeutic antibody, the use of the composition for increasing the efficiency of the therapeutic antibody, for increasing ADCC in a subject treated with a therapeutic antibody, or for treating a subject having disease, more particularly disease requiring the depletion of the targeted cells, preferably the diseased cells such as virally-infected cells, tumor cells or other pathogenic cells. Preferably, the disease is selected from the group consisting of a cancer, an auto-immune disease, an inflammatory disease, a viral disease. The disease also concerns a graft rejection, more particularly allograft rejection, and graft versus host disease (GVHD).

The therapeutic antibody can be bound by CD16, preferably through its Fc region. Preferably, the therapeutic antibody has a human IgG1 or an IgG3 Fc portion, particularly a monoclonal antibody or a fragment thereof, further preferably a human, humanized or chimeric antibody or a fragment thereof.

The compound, such as an antibody or a fragment thereof, that blocks the inhibitory receptor of a NK cell binds at least one of KIR or NKG2A/C human receptors and inhibits the related KIR2DL, KIR3DL and/or NKG2A/C-mediated inhibition of NK cell mediated cytotoxicity. Preferably, KIR2DL human receptor is selected from the group consisting of KIR2DL1, KIR2DL2, KIR2DL3 human receptors and KIR3DL human receptor is selected from the group consisting of KIR3DL1 and KIR3DL2.

In a preferred embodiment, the compound, such as an antibody or a fragment thereof, that blocks the inhibitory receptor of a NK cell binds at least one of the KIR2DL human receptors and inhibits the related KIR2DL-mediated inhibition of NK cell cytotoxicity. Preferably, KIR2DL human receptor is selected from the group consisting of KIR2DL1, KIR2DL2, KIR2DL3 human receptors. In a preferred embodiment, compound, such as an antibody or a fragment thereof, that blocks the inhibitory receptor of a NK cell binds a common determinant of KIR2DL human receptors and inhibits KIR2DL-mediated inhibition of NK cell cytotoxicity. More preferably, the compound, such as an antibody, binds a common determinant of KIR2DL1, KIR2DL2, KIR2DL3 human receptors and inhibits KIR2DL1-, KIR2DL2-, KIR2DL3-mediated inhibition of NK cell cytotoxicity. In a particular embodiment, the compound, such as an antibody, inhibits the binding of a HLA-C allele molecule having a Lys residue at position 80 to a human KIR2DL1 receptor, and the binding of a HLA-C allele molecule having an Asn residue at position 80 to human KIR2DL2 and KIR2DL3 receptors. In another particular embodiment, this antibody binds to the same epitope as monoclonal antibody DF200 produced by hybridoma DF200. Optionally, this antibody competes with monoclonal antibody DF200 produced by hybridoma DF200 for binding to a KIR receptor at the surface of a human. NK cell. In one preferred embodiment, the antibody is monoclonal antibody DF200 produced by hybridoma DF200.

The composition according to the present invention can comprise a combination of several compounds, preferably antibodies or a fragment thereof, that block different inhibitory receptors of NK cells. Preferably, compounds, preferably antibodies or a fragment thereof, that block inhibitory receptors of NK cells are specific of an inhibitory receptor selected from KIR2DL1, KIR2DL2, KIR2DL3, KIR3DL1, KIR3DL2, NKG2A and NKG2C and are able to inhibit the related KIR- or NKG2A/C-mediated inhibition of NK cell cytotoxicity. More preferably, the combination of "neutralizing" compounds is able to inhibit the KIR2DL1-, KIR2DL2-, and KIR2DL3-mediated inhibition of NK cell cytotoxicity.

Compositions of this invention may comprise any pharmaceutically acceptable carrier or excipient, typically buffer, isotonic solutions, aqueous suspension, optionally supplemented with stabilizing agents, preservatives, etc. Typical formulations include a saline solution and, optionally, a protecting or stabilizing molecule, such as a high molecular weight protein (e.g., human serum albumin).

According to the methods and compositions of the present invention, compounds, such as an antibody or a fragment thereof, that block the inhibitory receptor of a NK cell and therapeutic antibodies are administered in an efficient amount.

The efficient amount of therapeutic antibodies administered to the recipient can be between about 0.1 mg/kg and about 20 mg/kg. The efficient amount of antibody depends however of the form of the antibody (whole Ig, or fragments), affinity of the mAb and pharmacokinetics parameter that must be determined for each particular antibodies.

The efficient amount of compounds, such as an antibody or a fragment thereof, that block the inhibitory receptor of a NK cell administered to the recipient can be between about 0.1 mg/kg and about 20 mg/kg. The efficient amount of antibody depends however of the form of the antibody (whole Ig, or fragments), affinity of the mAb and pharmacokinetics parameter that must be determined for each particular antibodies. Typically, a full-length antibody would be administered once every two weeks, once every three weeks, or once every four weeks, while an antibody fragment could typically be administered more often, e.g., more than once a week or once a week.

The composition according to the present invention may be given by injection directly to a subject, typically by intravenous, intra-peritoneal, intra-arterial, intra-muscular or transdermic route. Several monoclonal antibodies have been shown to be efficient in clinical situations, such as Rituxan (Rituximab) or Xolair (Omalizumab), and similar administration regimens (i.e., formulations and/or doses and/or administration protocols) may be used with the composition of this invention.

Furthermore, the compositions of this invention may further comprise or may be used in combination with other active agents or therapeutic programs such as chemotherapy or other immunotherapies, either simultaneously or sequentially.

EXAMPLES

Example 1

Generation of a Pan KIR2DL Antibody

This Example describes the generation of murine monoclonal anti-KIR antibodies and the identification of DF200, a novel monoclonal antibody against a common determinant of KIR2DL human NK receptors.

Purification of PBLs and Generation of Polyclonal or Clonal NK Cell Lines

PBLs were derived from healthy donors by Ficoll Hypaque gradients and depletion of plastic adherent cells. To obtain enriched NK cells, PBLs were incubated with anti CD3, anti CD4 and anti HLA-DR mAbs (30 mns at 4° C.), followed by goat anti mouse magnetic beads (Dynal) (30 mns at 4° C.) and immunomagnetic selection by methods known in the art (Pende et al., J Exp Med. 1999; 190(10):1505-16. CD3 minus, CD4 minus DR minus cells are cultivated on irradiated feeder cells and 100 U/ml Interleukin 2 (Proleukin, Chiron Corporation) and 1.5 ng/ml Phytohemagglutinin A (Gibco BRL) to obtain polyclonal NK cell populations. NK cell are cloned by limiting dilution and clones of NK cells are characterized by flow cytometry for expression of cell surface receptors.

The following clones were used in this study

CP11, CN5 and CN505 are KIR2DL1 positive clones and are stained by EB6 or XA-141 antibodies.

CN12 and CP502 are KIR2DL3 positive clones and are stained by GL183 antibody.

Flow Cytometry Analysis mAbs used were produced in the laboratory JT3A (IgG2a, anti CD3), EB6 and GL183 (IgG1 anti KIR2DL1 and KIR2DL3 respectively), XA-141 IgM anti KIR2DL1 (same specificity as compared to EB6, anti CD4 (HP2.6), anti DR (D1.12, IgG2a). Instead of JT3A, HP2.6, and DR1.12, commercially available mAbs of the same specificities can be used for example from Beckman coulter Inc, Fullerton, Calif. EB6 and GL183 are commercially available in Beckman Coulter Inc, Fullerton, Calif. XA-141 is not commercially available but EB6 can be used for control reconstitution of lysis as described in Moretta (1993, supra).

Flow Cytometry

Cells were stained with the appropriate antibodies (30 mns at 4° C.) followed by PE or FITC conjugated polyclonal anti mouse antibodies (Southern Biotechnology Associates Inc). Samples were analysed by cytofluorometric analysis on a FACSAN apparatus (Becton Dickinson, Mountain View, Calif.).

Cytotoxicity Experiments

The cytolytic activity of NK clones was assessed by a standard 4 hr $^{51}$Cr release assay, in which effector NK cells were tested on Cw3 or Cw4 positive cell lines known for their sensitivity to NK cell lysis. All the targets are used at 5000 cells per well in microtitration plate and the Effector on target ratio is usually 4 effectors per target cells. The cytolytic assay is performed with or without supernatant of indicated monoclonal antibodies at a ½ dilution. The procedure is essentially the same as described in Moretta et al. (1993, supra).

Generation of New mAbs mAbs have been generated by immunizing 5 week old Balb C mice with activated polyclonal or monoclonal NK cell lines as described in Moretta et al. (J Exp Med. 1990; 171(3):695-714 and 1990; 172(6):1589-98, the disclosure of each of which is incorporated herein by reference. After different cell fusions, the mAbs were first selected for their ability to cross react with EB6 and GL183 positive NK cell lines and clones. Positive monoclonal antibodies were further screened for their ability to reconstitute lysis by EB6 positive or GL183 positive NK clones of Cw4 or Cw3 positive targets respectively.

Results

One of the monoclonal antibody, the DF200 mAb, was found to react with various members of the KIR family including KIR2DL1, KIR2DL2/3. Regarding the staining of NK cells with DF200 mAb both KIR2DL1+ and KIR2DL2/3+ cells were stained brightly.

NK clones expressing one or another (or even both) of these HLA class I-specific inhibitory receptors were used as effectors cells against target cells expressing one or more HLA-C alleles. As expected, KIR2DL1+NK clones displayed little if any cytolytic activity against target cells expressing HLA-Cw4 and KIR2DL3+NK clones displayed little or no activity on Cw3 positive targets. However, in the presence of DF200 mAb (used to mask their KIR2DL receptors) NK clones became unable to recognize their HLA-C ligands and displayed strong cytolytic activity on HLA-Cw3 or HLA-Cw4 positive targets.

For example, the C1R cell line (CW4+EBV cell line, ATCC n° CRL 1993) was not killed by KIR2DL1+ NK clones (CN5/CN5O$_5$), but the inhibition could be efficiently reverted by the use of either DF200 or a conventional anti KIR2DL1 mAb. On the other hand NK clones expressing the KIR2DL2/3+KIR2DL1-phenotype (CN12) efficiently killed C1R and this killing was unaffected by the DF200 mAb. Similar results can be obtained with KIR2DL2- or KIR2DL3-positive NK clones on Cw3 positive targets.

Example 2

Biacore Analysis of DF200 mAb/KIR 2DL1 and DF200 mAb/KIR 2DL3 Interactions

This Example describes an evaluation of the respective affinities of DF200 in binding to KIR2DL1 and KIR2DL3.

Production and Purification of Recombinant Proteins

The KIR 2DL1 and KIR 2DL3 recombinant proteins were produced in E. coli. cDNA encoding the entire extracellular domain of KIR 2DL1 and KIR 2DL3 were amplified by PCR from pCDM8 clone 47.11 vector (Biassoni et al, Eur J. Immunol. 1993; 23(5):1083-7; the disclosure of which is incorporated herein by reference) and RSVS(gpt)183 clone 6 vector (Wagtman et al., Immunity 1995 May; 2(5):439-49; the disclosure of which is incorporated herein by reference) respectively, using the following primers:

```
Sense:
                                         (SEQ ID NO: 3)
5'-GGAATTCCAGGAGGAATTTAAAATGCATGAGGGAGTCCACAG-3'

Anti-sense:
                                         (SEQ ID NO: 4)
5'-CCCAAGCTTGGGTTATGTGACAGAAACAAGCAGTGG-3'
```

They were cloned into the pML1 expression vector in frame with a sequence encoding a biotinylation signal (Saulquin et al, 2003; the disclosure of which is incorporated herein by reference).

Protein expression was performed into the *E. coli* BL21 (DE3) bacterial strain obtained from Invitrogen. Transfected bacteria were grown to $OD_{600}=0.6$ at 37° C. in medium supplemented with ampicillin (100 µg/ml) and induced with 1 mM IPTG.

Proteins were recovered from inclusion bodies under denaturing conditions (8 M urea). Refolding of the recombinant proteins was performed in Tris 20 mM, pH 7.8, NaCl-150 mM buffer containing L-arginine (400 mM, Sigma) and β-mercaptoethanol (1 mM), at RT, by decreasing the urea concentration in a six step dialysis (4, 3, 2, 1, 0.5 and 0 M urea, respectively). Reduced and oxidized glutathion (5 mM and 0.5 mM respectively, Sigma) were added during the 0.5 and 0 M urea dialysis steps. Finally, the proteins were dialyzed extensively against Tris 10 mM, pH 7.5, NaCl 150 mM buffer. Soluble refolded proteins were concentrated and then purified on a Superdex 200 size-exclusion column (Pharmacia; AKTA system).

Biacore Analysis.

Surface plasmon resonance measurements were performed on a Biacore apparatus (Biacore).

In all Biacore experiments HBS buffer supplemented with 0.05% surfactant P20 served as running buffer.

Protein Immobilisation.

Recombinant KIR 2DL1 and KIR 2DL3 proteins were immobilized covalently to carboxyl groups in the dextran layer on a Sensor Chip CM5 (Biacore). The sensor chip surface was activated with EDC/NHS(N-ethyl-N'-(3-dimethylaminopropyl)carbodiimidehydrochloride and N-hydroxysuccinimide, Biacore). Proteins, in coupling buffer (10 mM acetate pH 4.5) were injected. Deactivation of the remaining activated groups was performed using 100 mM ethanolamine pH8 (Biacore).

Affinity Measurements.

For kinetic measurements, various concentrations of the soluble antibody ($10^{-7}$ to $4 \times 10^{-10}$ M) were applied onto the immobilized sample. Measurements were performed at 20 µl/min continuous flow rate. For each cycle, the surface of the sensor chip was regenerated by 5 µl injection of 10 mM NaOH pH 11.

The BIAlogue Kinetics Evaluation program (BIAevaluation 3.1, Biacore) was used for data analysis.

Results

TABLE 1

BIAcore analysis of DF200 mAb binding to immobilized KIR 2DL1 and KIR 2DL3

| Antigen | KD ($10^{-9}$ M) |
|---|---|
| KIR 2DL1 | 10.9 +/− 3.8 |
| KIR 2DL3 | 2.0 +/− 1.9 |

KD: Dissociation constant.

The soluble analyte (40 µl at various concentrations) was injected at a flow rate of 20 µl/min in HBS buffer, on a dextran layers containing 500 or 540 reflectance units (RU), and 1000 or 700 RU of KIR 2DL1 and KIR 2DL3 respectively. Data are representative of 6 independent experiments.

Example 3

Enhancement of ADCC by Using a Combination of Rituxan and Anti-KIR mAb

This experiment shows that Rituxan alone mediates essentially no ADCC by a KIR2DL1-positive NK clone on Cw4-positive target cells, while the ADCC of the KIR2DL1-positive clone is greatly enhanced in the presence of an anti-KIR2DL1 antibody.

Preparation of Human Nk Clones

Blood mononuclear cells depleted of T cells by negative anti-CD3 immuno-magnetic selection (Miltenyi) are plated under limiting-dilution conditions, activated with phytohemagglutinin (PHA) (Biochrom KG, Berlin, Germany), and cultured with interleukin (IL)-2 (Chiron B.V., Amsterdam, Netherlands) and irradiated feeder cells. Cloning efficiencies are equivalent in all donors and range between 1 in 5 and 1 in 10 plated NK cells. Cloned NK cells are screened for alloreactivity by standard $^{51}$Cr release cytotoxicity against Epstein-Barr virus-transformed B lymphoblastoid cell lines of known HLA type at an effector to target ratio of 10:1. Clones exhibiting ≥30% lysis were scored as alloreactive. As a rule, clones either exhibit <5% or >40% lysis.

Enhancement of ADCC Mediated by Rituxan by a KIR2DL1 Positive NK Cell Clone

The cytolytic activity of NK clone is assessed by a standard 4 hr $^{51}$Cr release assay, in which effector NK cells were tested on HLA-Cw3 or HLA-Cw4 positive EBV cell lines (CD20 positive), known for their sensitivity to NK cell lysis. All the targets are used at 5000 cells per well in microtitration plate and a certain Effector (NK cell clone) on target ratio. In certain experiments, the therapeutic chimeric anti CD20 rituximab (Rituxan, Idec) is added at 5 µg/ml is added to the effector target mixture. In certain experiments, the EB6 antibody (anti KIR2DL1) at 10 µg/ml is added to the effector target mixture.

This experiment showed that Rituxan alone mediates essentially no ADCC by the KIR2DL1 positive NK clone on Cw4 positive target. ADCC of KIR2DL1 positive clone is greatly enhanced in the presence of anti KIR2DL1 antibody.

Example 4

Enhancement of NK-Mediated Killing of Virus Infected Cells

Anti-KIR mAbs are tested for their ability to enhance NK-mediated killing of virus infected cells by standard Chromium-51 ($^{51}$Cr)-release assays (cytotoxicity assays).

$^{51}$Cr assays are well known in the art. In the context of the present invention, the $^{51}$Cr-release assays are generally performed in one of two configurations, depending on whether the aim is to test whether 1) anti-KIR mAbs by themselves enhance NK-mediated killing of virus-infected cells or 2) whether anti-KIR mAbs enhance the efficacy of other therapeutic mAbs to induce killing of target cells expressing the ligand of another therapeutic mAb. The only difference between these two general configurations is related to the choice of the precise NK cell population and the target cell population. By way of example, the following method describes how to test whether an anti-KIR mAb can enhance the efficacy of other therapeutic mAbs used in anti-viral therapy, in this case anti-CD4 mAbs being developed for HIV treatment. Anti-CD4 mAbs bind to CD4 on T cells, infected or not by HIV, and at the same time can bind CD16, the activating Fc receptor on NK cells, thereby stimulating NK cells to kill CD4-expressing target cells. However, this stimulatory effect is counter-balanced by inhibitory signaling via KIR, upon engagement of HLA-C. When both an anti-CD4 and an anti-KIR mab are added to the $^{51}$Cr-assay at the same time, the level of killing is higher than if anti-CD4 is added alone. The experiment is performed with the NK cell line called YTS-2DL1 which does not lyse the B cell-line 721.221 transfected with HLA-C and CD4, because HLA-Cw4 provides protection by delivering inhibitory signaling to the NK cell, via KIR.

The target cells are labeled with $^{51}$Cr for 1 hr at 37° C., washed, and plated at 5000 cells/well in 96-well bottom plates, together with various numbers of NK cells, to give effector:target ratios of 0, 3:1, 1:1, 3:1 and 9:1. Then an anti-CD4 mAb is added by itself, at different concentrations from 1-50 ug/ml (final concentration), or at the same concentrations together with 1 ug/ml of an anti-KIR mAb. The plate is incubated at 37° C. for 4 hrs, centrifuged, and the supernatant harvested and counted. The amount of $^{51}$Cr in the supernatant is proportional to the amount of target-cell killing that has taken place. In this experiment, the same level of killing is obtained after incubation with 50 ug/ml of anti-CD4 as with 2 ug/ml of anti-CD4 plus 1 ug/ml of anti-KIR mAb, demonstrating that the anti-KIR mAb significantly enhances the efficacy of the anti-CD4 mAbs. A similar enhancement of the ability of anti-CD4 mAbs to induce cell-killing is expected when using HIV-infected cells as targets, since the mechanism is the same, but due to safety concerns the experiments are preferentially performed with un-infected cells.

Example 5

Anti-KIR Antibody-Promoted Killing of HIV-Infected Target Cells

NK cells are important in the control of viral infections. In HIV-infected patients with AIDS, reductions in the numbers and function of NK cells have been reported. In previous studies, an increased expression of killer Ig-like receptors (KIR) has been seen in HIV patients with controlled disease. KIRs are expressed on NK-cells and T-cells and recognize MHC class I molecules on target cells. Interaction between KIRs and their ligands on target cells can either lead to inhibition or activation of the NK-cells, depending on the type of KIR molecule. It has previously been shown that KIR-ligand mismatched NK-cells can kill tumor targets.

In this example, to test whether inhibitory KIR may control NK killing of HIV-infected targets, and whether killing may be augmented by blocking of KIR using mAbs, the interaction between KIRs and MHC class I molecules were blocked with an anti-KIR antibody. The effect of this treatment was measured by the expression on NK cells of a degranulation marker called CD107a, whose expression level is proportional to killing by NK cells. An increased degranulation was observed in NK cells both from healthy individuals and HIV infected patients when the KIR interaction between NK-cells and HLA-C expressing cell lines was blocked using the anti-KIR antibody 1-7F9, demonstrating that NK cells from this patient population are functional, and activatable when KIR is blocked. These results show that activation of NK cells by blocking inhibitory KIRs could potentially be a new immunotherapeutic treatment for HIV infected patients.

Blood Samples

Blood was received from 11 healthy individuals as well as 10 HIV-1 infected patients from Venhälsan at Södersjukhuset in Stockholm. All of the patients were male and of the healthy controls three were male and seven female. All of the patients were on highly active antiretroviral therapy (HAART) treatment and had a controlled viremia, with six of the patients having a viral load of <50 RNA copies/ml and the rest had a viral load of between 77 and 200 RNA copies/ml. The median CD4+ count for the HIV-1 infected patients was 582 CD4+ cells/µl (range 248-1043). PBMCs were purified by density centrifugation.

Antibodies

The following antibodies were purchased from BD Biosciences and used for FACS staining, IgG2b anti-human CD56 (NCAM 16.2) FITC, IgG1 anti-human CD3 (SK7) PerCP, IgG1 anti-human CD56 (B159) APC, anti-human CD56 (leu-19) PE, anti-human KIR (NKB1) FITC, purified IgG1 mouse anti-human CD107a (H4A3) and IgG1 mouse anti-human CD107a (H4A3) FITC. Anti-human KIR2DL1 (CD158a) and anti-human KIR2DL2 (CD158b) from Immunotech. The human anti-KIR(1-7F9) mAb, specific for KIR2DL1, 2, and -3, as well as KIR2DS1 and -2 has been described in WO2005003168 and WO2005003172. Anti-human IgG4 FITC from Southern Biotech was used as secondary antibody for detection of 1-7F9.

NK Receptor Staining 500.000 fresh PBMCs were stained for 30 min at 4° C. with unlabelled antibodies. Cells were washed in PBS+1% FCS and then stained with the secondary Ab for 10 min at 4° C. After washing, the cells were blocked with PBS+1% mouse serum. Cells were then stained for 10 min at 4° C. with conjugated antibodies against various NK-receptors and CD56 and CD3. Cells were fixed in PBS with 1% FCS and 1% paraformaldehyde and saved at 4° C. until analyzed in a four colour FACS Calibur. The results were analyzed by Cell Quest Pro.

The CD107a Assay

Fresh PBMCs stimulated overnight with 200 U/ml IL-2 (Peprotech) in RPMI medium supplemented with PEST and 10% fetal calf serum (FCS) were added to a 96-well plate. The cells were blocked for background expression of CD107a by addition of 5 µg/ml unmarked purified CD107a mAb (BD). After 15 min incubation at room temperature, cells were washed three times with complete RPMI medium. In some instances, PBMCs were pre-incubated for 30 min at RT with 100 µg/ml anti-KIR antibody. Target cells (K562, 721.221, 721.Cw3, 721.Cw4, 721.Cw6, CEM or autologous CD4+ cells) were added at an effector:target ratio of 2:1, with 500.000 effector cells and 250.000 target cells per well. As a negative control PBMCs were incubated with complete medium. To a total volume of 250 µl, 4 µl anti-human CD107a FITC labelled mAb and GolgiStop (BD) was added. Cells were quickly spun down at 500 rpm for 1 min to promote effector and target cell contact. After 4 h incubation at 37° C. the cells were washed in PBS+1% FCS and then stained for the surface markers CD56 and CD3 for 10 min at 4° C. Cells were washed and fixed with 1% paraformaldehyde and then analysed in the FACS Calibur instrument.

Target Cells

Target cells used for the CD107a assay were the MHC class I defective cell lines K562 and 721.221 as positive controls, and the MHC class I expressing cell lines 721.Cw3, 721.Cw4 and 721.Cw6 transfected with different HLA-C alleles. The T-cell line CEM was used as a target cell since it is susceptible to HIV-1 infection. All cell lines were grown in RPMI medium supplemented with PEST and 10% FCS.

Autologous CD4+ T-cells were purified from fresh PBMCs by StemSep® Human CD4+ T-cell Enrichment Cocktail and Magnetic Colloids according to the manufacturer's description (StemCell Technologies). LS separation columns and a MidiMACS magnet from Miltenyi Biotec were used for the separation step. The CD4+ T-cells were stimulated for 3 days in RPMI medium supplemented with 20 U/ml IL-2 (Peprotech) and 5 µg/ml PHA (Oxoid, Sollentuna, Sweden), PEST and 10% FCS. The cells were washed in medium and then stimulated with 10 U/ml IL-2 for 12 more days before use as target cells in the CD107a assay.

HIV-1 Infection of Target Cells

CEM cells were infected with HIV-1 IIIB (LAI) at a 1000× TCID50 by incubation of cells and virus for 4 h at 37° C., slowly shaking at 100 rpm. The cells were suspended in warm medium and centrifuged for 8 min at 1000 rpm, the washing was repeated once and then the cells were kept in 24-well plates at 37° C. for 12 days. Every 3-4 day fresh medium was added to the cultures. The cells were stained for intracellular p24 expression in order to determine if the cells were infected. 500 000 cells were washed in PBS+1% FCS and stained with anti-human CD4 APC for 10 min at 4° C. After washing cells were fixed by incubation for 20 min at 4° C. with 100 µl BD Cytofix/Cytoperm solution and then cells were washed twice in BD Perm/Wash solution. The IgG1 mouse anti-p24 Ab, KC57 FITC (Beckman Coulter) or isotype control, diluted 1/20 in BD Perm/Wash solution was added. After 45 min incubation at 4° C. cells were washed in BD Perm/Wash solution again and then fixed in PBS with 1% PFA and 1% FCS before analyzed in the FACS Calibur.

Statistics

Results from healthy controls and HIV-1 infected patients were compared statistically by the non-parametric Mann-Whitney U test (Wilcoxon rank sum test).

Results

Changed Expression of NK-Cell Receptors in HIV-1 Infected Individuals

To investigate the effects of HIV-1 infection on receptor expression on NK cells, freshly purified PBMC were stained for CD56 and CD3 (FIG. 1a), as well as for several different NK receptors. The proportion of CD56+CD3− NK cells did not differ significantly (P=0.06) between HAART treated HIV-1 infected patients and healthy controls, although the median was decreased in HIV-1 infected patients (FIG. 1b). NK cells can be divided into CD56bright and CD56dim cells (FIG. 1a). In this study a slight decrease in CD56dimCD3− cells could be seen for HIV-1 infected patients compared to healthy controls, but the difference was not significant.

Figure 2:
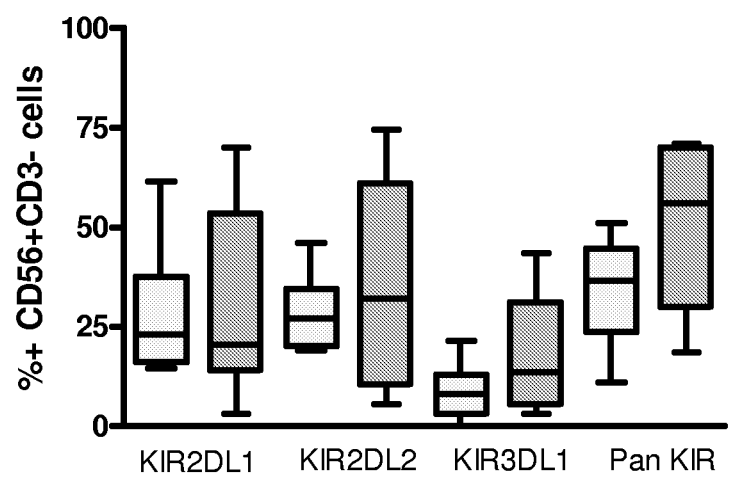
FIG. 2. Percentage of KIR expressing NK-cells in healthy controls (white boxes) and HIV-1 infected patients (grey boxes), P>0.05 for all KIRs. The antibodies against KIR2DL1, KIR2DL2 and KIR3DL1 recognise different KIR receptors and the Pan KIR antibody 1-7F9 recognises KIR2DL/S1, KIR2DL/S2 and KIR2DL3.

The expression of a panel of different NK receptors on CD56+CD3-NK-cells was analyzed. Although not significant, an increased median in the expression of KIR receptors was seen in HIV-1 infected patients (FIG. 2). Four different mAbs for KIRs were used, of which three are specific for single KIRs (KIR2DL1, KIR2DL2 and KIR3DL1) and one, 1-7F9, is cross-reactive with KIR2DL/S1, KIR2DL/S2 and KIR2DL3.

Activity of NK-Cells Measured by CD107a Expression

Figure 3:
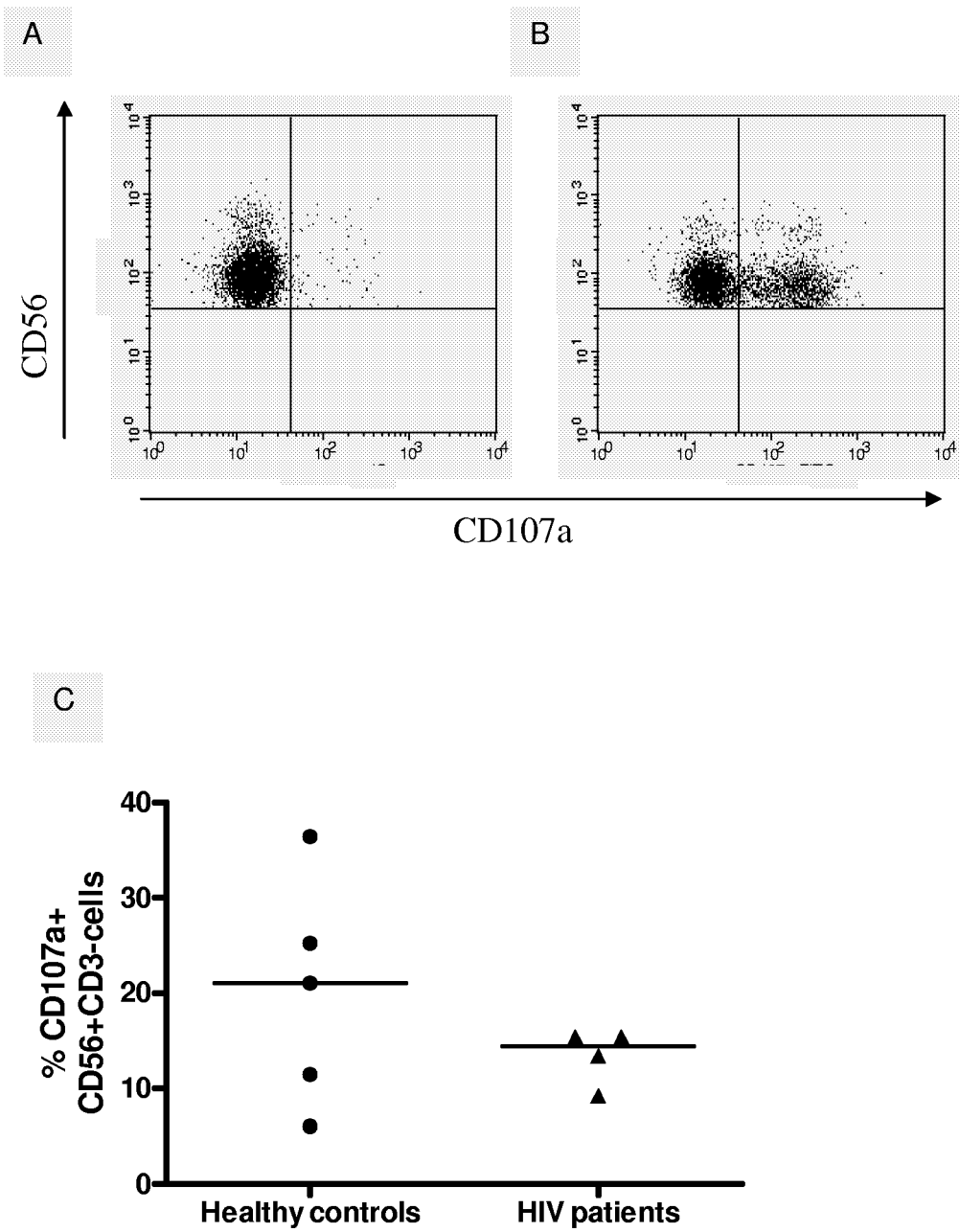
FIG. 3. Expression of the degranulation marker CD107a in gated CD56+CD3–NK– cells without stimulation (A) and after stimulation with the NK-sensitive K562 cell line (B). (C) The percent expression of CD107a after stimulation with K562 cells is shown for healthy controls as well as for HIV-1 infected patients. There was no significant difference between the groups. Median for each group is shown.

PBMCs from HIV-1 infected patients and healthy controls were stimulated with NK-sensitive K562 target cells, which lead to an increase in cell-surface density of the degranulation marker CD107a (FIG. 3 a,b), reflecting killing of K562 target cells by the NK cells. The median percentage of CD107a+ CD56+CD3− cells was only marginally higher for healthy controls than for HIV-1 infected patients after stimulation with K562 cells, (FIG. 3c), indicating only slightly decreased function of NK cells in HIV-1 infected patients, although the difference was not statistically significant.

Blocking of KIRs Increase CD107a Expression

Figure 4:
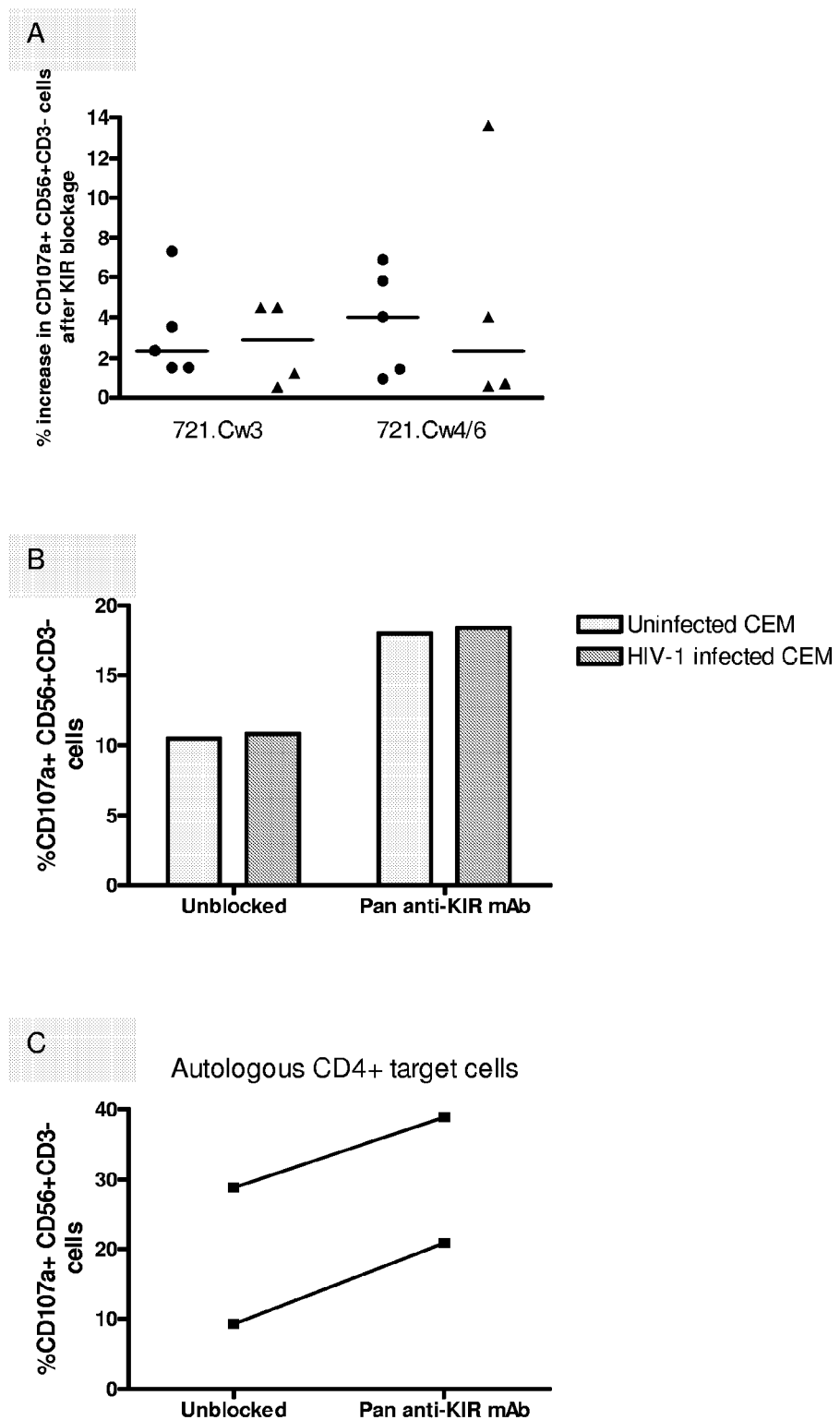
FIG. 4. (A) The percent increased expression of CD107a in NK-cells, after stimulation with 721.221 cells transfected with different HLA-C alleles and blockage of all KIRs with the anti-KIR mAb 1-7F9, is shown. The anti-KIR mAb induced CD107 to a similar extent in (1) NK cells expressing KIR2DL2 and stimulated with cells transfected with HLA-Cw3 as in (2) NK cells expressing KIR2DL1 and challenged with target cells transfected with HLA-Cw4 or HLA-Cw6, both binding to KIR2DL1. Also, no significant difference between healthy individuals (circles) and HIV-1 infected patients (triangles) could be seen. The median for each group is shown. (B) Blocking of all KIRs on NK-cells stimulated with the uninfected CEM cell line (white bars) or 70% HIV-1 infected CEM cells (grey bars) increases CD107a expression. No difference between uninfected and HIV-1 infected cells could be seen in this experiment performed once with healthy control PBMC. (C) Autologous CD4+ cells, expanded and activated with IL-2 and PHA, were used as targets and blockage of KIRs on NK-cells with anti-KIR(1-7F9) mAb lead to a 10% increased CD107a expression in two independent experiments with blood from healthy individuals.

To investigate if it is possible to use the CD107 assay for detecting increased NK-mediated killing of HLA-C expressing cells in response to blocking inhibitory KIR receptors, we blocked the KIR receptors with the human 1-7F9 antibody (IgG4) which binds to all inhibitory KIR2DL receptors, and measured upregulation of CD107a in response to HLA-C positive tumor cell lines. The assay was performed with or without blockage of the KIR receptors. When 721.221 cells transfected with different HLA class 1 molecules were used as target cells an increased expression of CD107a could be seen when the KIR receptors were blocked. The increased expression of CD107a on NK cells was not different between HIV-1 infected patients and healthy controls and it ranged from 0.5-13.6% (FIG. 4a).

Since it was possible that HIV-infected cells may express lower levels of ligands for activating NK receptors, and be less sensitive to NK-mediated killing than un-infected cells, we next tested whether it was possible to get an effect of blocking KIRs when the target cells were HIV-1 infected. The T cell line called CEM, which is susceptible to HIV-1 infection, was infected with the HIV-1 IIIB strain. Uninfected and 70% infected CEM cells (as determined by p24 FACS staining) were used as targets in the CD107a assay and PBMCs from a healthy individual were used as effector cells. As can be seen in FIG. 4b, blocking of KIRs using the 1-7F9 antibody induced a similar increase in CD107a expression in both the un-infected and HIV-infected cells. These results suggest that HIV-infected cells retain expression of ligands for activating NK receptors, and that the expression of HLA-C provide protection from lysis. Anti-KIR mAbs can be used to interfere with this protection, rendering HIV-infected cells sensitive to NK killing.

To find out if KIR blockage of NK-cells also can cause an effect against autologous healthy CD4+ cells we used non-infected autologous CD4+ cell blasts, expanded in IL-2 and activated with PHA, as targets. Blocking of KIRs by pre-incubating NK cells with 1-7F9 increased the expression of CD107a on NK cells with about 10% in two independent experiments with lymphocytes from healthy individuals (FIG. 4c). This low level of cytotoxicity against healthy target cells is consistent with the requirement for engagement of activating NK receptors by stress-inducible activation ligands on target cells, which are not generally present on healthy targets. However, it is possible that the culture of CD4 blasts in PHA plus IL-2 led to low-level expression of some activation-ligands on some target cells.

The results of this study show that NK cells from HIV patients treated with HAART are largely comparable to NK cells from healthy donors with respect to phenotype and activity. Most importantly, the experiments described in this invention indicate that NK cells in patients treated with HAART are under negative regulation by inhibitory KIR, and the activity of such NK cells can be enhanced by blocking KIR with anti-KIR mAbs. Accordingly, this patient group would be a good target population for treatment with anti-KIR mAbs. In contrast, patients with very active disease have impaired NK cells, which might not be activatable even if you "remove the KIR-brake" with, e.g., an anti-KIR antibody.

All references, including publications, patent applications and patents, cited herein are hereby incorporated by reference to the same extent as if each reference was individually and specifically indicated to be incorporated by reference and was set forth in its entirety herein.

All headings and sub-headings are used herein for convenience only and should not be construed as limiting the invention in any way, Any combination of the above-described elements in all possible variations thereof is encompassed by the invention unless otherwise indicated herein or otherwise clearly contradicted by context.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents, The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

The invention claimed is:

1. A method of treatment of a viral disease caused by human immunodeficiency virus (HIV) in a human subject in need thereof, comprising administering to a human subject that has been treated with highly active antiretroviral therapy (HAART) a composition comprising a first compound, said first compound being an antibody that binds specifically to a natural killer cell immunoglobulin-like receptor (KIR) selected from the group consisting of KIR2DL1, KIR2DL2, and KIR2DL3, and blocks KIR2DL1-, KIR2DL2-, and KIR2DL3-mediated inhibition of natural killer (NK) cell cytotoxicity.

2. The method of claim 1, wherein the antibody competes with monoclonal antibody DF200 in binding to at least one of KIR2DL1, KIR2DL2, and KIR2DL3.

3. The method of claim 1, wherein the antibody competes with an antibody comprising variable heavy (VH) and variable light (VL) chains having the sequences set forth in SEQ ID NO:1 and SEQ ID NO:2, respectively, in binding to at least one of KIR2DL1, KIR2DL2, and KIR2DL3.

4. The method of claim 3, wherein the antibody comprises variable heavy (VH) and variable light (VL) chains having the sequences set forth in SEQ ID NO:1 and SEQ ID NO:2, respectively.

5. The method of claim 1, wherein the human subject has been treated with HAART for a sufficient period of time to achieve an HIV plasma level below a predetermined level prior to administering the first compound.

6. The method of claim 4, further comprising administering to the subject a second compound which is a therapeutic antibody or fusion protein binding an antigen expressed on an HIV-infected cell.

7. The method of claim 6, wherein the second compound is a therapeutic antibody.

* * * * *

UNITED STATES PATENT AND TRADEMARK OFFICE
CERTIFICATE OF CORRECTION

| | | |
|---|---|---|
| PATENT NO. | : 8,551,483 B2 | Page 1 of 1 |
| APPLICATION NO. | : 11/813399 | |
| DATED | : October 8, 2013 | |
| INVENTOR(S) | : Wagtmann et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1588 days.

Signed and Sealed this
Seventeenth Day of February, 2015

Michelle K. Lee
*Deputy Director of the United States Patent and Trademark Office*